(12) United States Patent
Hammer et al.

(10) Patent No.: US 12,396,795 B2
(45) Date of Patent: Aug. 26, 2025

(54) COMBINING MULTIPLE ERGONOMIC RISK FACTORS IN A SINGLE PREDICTIVE FINITE ELEMENT MODEL

(71) Applicant: The Boeing Company, Chicago, IL (US)

(72) Inventors: Liisa Charlie Hammer, Seattle, WA (US); Karen C. Takatani, Renton, WA (US); Kevin F. Malik, Seattle, WA (US); Geoffrey A. Butler, Seattle, WA (US); Robert Courdji, Everett, WA (US)

(73) Assignee: THE BOEING COMPANY, Arlington, VA (US)

( * ) Notice: Subject to any disclaimer, the term of this patent is extended or adjusted under 35 U.S.C. 154(b) by 763 days.

(21) Appl. No.: 17/657,177

(22) Filed: Mar. 30, 2022

(65) Prior Publication Data

US 2022/0338928 A1 Oct. 27, 2022

Related U.S. Application Data

(60) Provisional application No. 63/180,353, filed on Apr. 27, 2021.

(51) Int. Cl.
*A61B 34/10* (2016.01)
*A61B 8/00* (2006.01)

(52) U.S. Cl.
CPC .............. *A61B 34/10* (2016.02); *A61B 8/485* (2013.01)

(58) Field of Classification Search
CPC ....... A61B 34/10; A61B 8/485; A61B 5/0037; A61B 5/055; A61B 2503/20;
(Continued)

(56) References Cited

U.S. PATENT DOCUMENTS 9,610,036 B1 4/2017 De Sapio et al.
2003/0135129 A1 7/2003 Cusimano et al.
(Continued)

FOREIGN PATENT DOCUMENTS

EP 2839772 A1 2/2015
JP 2011141706 A 7/2011
(Continued)

OTHER PUBLICATIONS

Edwards 2018 Exerc. Sport. Sci. Rev. 46:224-231 (Year: 2018).*
(Continued)

*Primary Examiner* — Keith M Raymond
*Assistant Examiner* — Patrick M Mehl
(74) *Attorney, Agent, or Firm* — MH2 Technology Law Group LLP

(57) ABSTRACT

A method for modeling soft tissue includes receiving one or more images showing an anatomical geometry of a first subject. The anatomical geometry includes a soft tissue. The method also includes measuring a plurality of parameters of the anatomical geometry of the first subject using one or more sensors attached to the first subject. The method also includes receiving a first set of material properties for the soft tissue of the first subject, a second subject, or both. The method also includes identifying a second set of material properties that characterizes the soft tissue while the first subject performs a task. The method also includes determining a strain on the soft tissue, a stress on the soft tissue, or both based at least partially upon the one or more images, the parameters, the first set of material properties, and the second set of material properties.

20 Claims, 12 Drawing Sheets

(58) Field of Classification Search
CPC ... A61B 5/1122; A61B 5/4884; A61B 5/4533; A61B 5/4576; A61B 5/4523; A61B 5/45; A61B 5/6823; A61B 5/6824; G16H 20/30; G16H 20/40; G16H 30/40; G16H 50/50

See application file for complete search history.

(56) References Cited

U.S. PATENT DOCUMENTS

| | | |
|---|---|---|
| 2017/0055836 A1 | 3/2017 | Thelen et al. |
| 2021/0174929 A1 | 6/2021 | Bruchal et al. |
| 2022/0192637 A1 | 6/2022 | Kirby et al. |
| 2022/0230732 A1 | 7/2022 | Hammer et al. |
| 2023/0067316 A1 | 3/2023 | Hammer et al. |

FOREIGN PATENT DOCUMENTS

| | | |
|---|---|---|
| WO | 2014201020 A1 | 12/2014 |
| WO | 2021113725 A1 | 6/2021 |

OTHER PUBLICATIONS

Murakami et al. 2021 International Journal of Fatigue 146: article 106138, 14 pages; ePub. Date Jan. 5, 2021 (Year: 2021).*

Pizzolato et al. 2017 Front. Comput. Neurosci. 11: article 96, 16pages (Year: 2017).*

Office Action issued on Jun. 25, 2024, for Japanese Application No. 2022-534139, including English machine translation, 8 pages.

Garg, A., et al., "Applications of biomechanics for prevention of work-related musculoskeletal disorders," Ergonomics, vol. 52, No. 1, Jan. 2009, pp. 36-59.

Crisan, Carmen-Clara (PCT Authorized Officer), Notification of Transmittal of the International Search Report and the Written Opinion of the International Searching Authority, or the Declaration, mailed Jul. 19, 2022, for International Application No. PCT/US2022/022473, 22 pages.

Huber, G., et al., "Dependence of spinal segment mechanics on age and posture," Research Project F 2069—Bundesanstalt für Arbeitsschutz und Arbeitsmedizin, May 3, 2010, pp. 1-173.

Qasim, M., et al., "Initiation and progression of mechanical damage in the intervertebral disc under cyclic loading using continuum damage mechanics methodology: A finite element study," Journal of Biomechanics, vol. 45, No. 11, Jul. 26, 2012 (Published online Jun. 8, 2012), pp. 1934-1940.

Weiss, J.A., et al., "Three-dimensional finite element modeling of ligaments: Technical aspects," Medical Engineering & Physics, vol. 27, No. 10, Aug. 8, 2005, pp. 845-861.

Zhang, Q., et al., "Techniques for In Vivo Measurement of Ligament and Tendon Strain: A Review," Annals of Biomedical Engineering, vol. 49, No. 1, Jan. 2021 (Published online Oct. 6, 2020), pp. 7-28.

Doherty, F. (PCT Authorized Officer), Notification Concerning Transmittal of International Preliminary Report on Patentability and Written Opinion of the International Searching Authority mailed Nov. 9, 2023, for International Application No. PCT/US2022/022473, 15 pages.

Buckley, M.R., et al., "Validation of an Empirical Damage Model for Aging and In Vivo Injury of the Murine Patellar Tendon," Journal of Biomechanical Engineering, vol. 135, Apr. 2013, pp. 041005-1-041005-7.

Colombini, D., et al., "Preventing upper limb work-related musculoskeletal disorders (UL-WMSDS): New approaches in job (re)design and current trends in standardization," Applied Ergonomics, vol. 37, No. 4, Jul. 2006, pp. 441-450.

Fung, D.T., et al., "Subrupture Tendon Fatigue Damage," Journal of Orthopaedic Research, vol. 27, Feb. 2009 (Published online Aug. 6, 2008), pp. 264-273.

Takatani, K.C., et al., "A new approach to prevent overuse injuries of the rotator cuff supraspinatus tendon using the cumulative fatigue concept," Theoretical Issues in Ergonomics Science, vol. 18, No. 5, 2017 (Published online Jun. 22, 2017), pp. 455-476.

Van Eerd, D., et al., "Effectiveness of workplace interventions in the prevention of upper extremity musculoskeletal disorders and symptoms: an update of the evidence," Occup. Environ. Med., vol. 73, 2016 (Published Online First Nov. 9, 2015), pp. 62-70.

Daneshmandi, H., et al., "An ergonomic intervention to relieve musculoskeletal symptoms of assembly line workers at an electronic parts manufacturer in Iran," Work, vol. 61, 2018, pp. 515-521.

Extended European Search Report for European Application No. 21215965.1 dated Jun. 8, 2022 (11 pages).

De Sapio, V., et al., "Demographic Specific Musculoskeletal Models of Factory Worker Performance, Fatigue, and Injury," 2016 IEEE Aerospace Conference, IEEE, Mar. 5, 2016, pp. 1-13.

Golze, Doreen (PCT Authorized Officer), Notification of Transmittal of the International Search Report and the Written Opinion of the International Searching Authority (Forms PCT/ISA/220, PCT/ISA/210 and PCT/ISA/237) for International Application No. PCT/US2020/063430 dated Mar. 26, 2021 (15 pages).

Kim, Y.-S., et al., "In Vivo Strain Analysis of the Intact Supraspinatus Tendon by Ultrasound Speckles Tracking Imaging," Journal of Orthopaedic Research, Dec. 2011, 29(12):1931-1937.

Klauser, A.S., et al., "Sonoelastography: Musculoskeletal Applications," Radiology, Sep. 2014, 27(3): 622-633.

Lake, S.P., et al., "Effect of Fiber Distribution and Realignment on the Nonlinear and Inhomogeneous Mechanical Properties of Human Supraspinatus Tendon Under Longitudinal Tensile Loading," NIH Public Access Author Manuscript, J. Orthop. Res., Dec. 2009, 27(12):1596 (17 pages).

Lindner, Nora (PCT Authorized Officer), Notification Concerning Transmittal of International Preliminary Report on Patentability (Form PCT/IB/373) for International Application No. PCT/US2020/063430 dated Jun. 16, 2022 (8 pages).

Prado-Costa, R., et al., "Ultrasound elastography: compression elastography and shear-wave elastography in the assessment of tendon injury," Insights into Imaging, 2018 (Published online Aug. 17, 2018), 9:791-814.

Qasim, M., et al., "Initiation and Progression of Mechanical Damage in the Intervertebral Disc Under Cyclic Loading Using Continuum Damage Mechanics Methodology: A Finite Element Study," Journal of Biomechanics, Jun. 2012, 45(11):1934-1940.

Rabello, L.M., et al., "Substantiating the Use of Ultrasound Tissue Characterization in the Analysis of Tendon Structure: A Systematic Review," www.cjsportmed.com, Clin. J. Sport Med., May 2021, 31(3):e161-e175.

Schechtman, H., et al., "In Vitro Fatigue of Human Tendons," J. Biomechanics, Aug. 1997, 30(8):829-835.

Van Schie, H.T.M., et al., "Efficacy of computerized discrimination between structure-related and non-structure-related echoes in ultrasonographic images for the quantitative evaluation of the structural integrity of superficial digital flexor tendons in horses," Am. J. Vet. Res., Jul. 2001, 62(7):1159-1166.

Van Schie, H.T.M., et al., "Ultrasonographic Tissue Characterisation of Human Achilles Tendons: Quantification of Tendon Structure Through a Novel Non-Invasive Approach," Br. J. Sports Med., Dec. 2010 (Published online Aug. 6, 2009), 44(16):1153-1159.

Tse, K.M., et al., "A review of head injury and finite element head models," American Journal of Engineering, Technology and Society, vol. 1, No. 5, Dec. 2014, pp. 28-52.

Office Action mailed in CA 3,158,278 on Feb. 19, 2024. (5 Pages).

Violante, Karen (AU Examiner), Examination Report No. 1 for Standard Patent Application, issued Jun. 13, 2025 in related Australian Patent No. 202039817, 4 pages.

* cited by examiner

COMBINING MULTIPLE ERGONOMIC RISK FACTORS IN A SINGLE PREDICTIVE FINITE ELEMENT MODEL

CROSS-REFERENCE TO RELATED APPLICATIONS

This application claims priority to U.S. Provisional Patent Application No. 63/180,353, filed on Apr. 27, 2021, the entirety of which is incorporated by reference herein.

FIELD

The subject matter described herein generally relates to the field of material science and its application to ergonomics. More particularly, the subject matter disclosed herein relates to soft tissue material repetitive stress injuries and guidelines to minimize the risk of sustaining such injuries.

BACKGROUND

Overuse injuries, particularly of the shoulder, including the supraspinatus tendon, are some of the most significant of ergonomics injuries. Accordingly, there is a need to understand the dynamics of workplace or other activities that contribute to and can result in stress, for example to a tendon, to address a task or repetition of tasks that contribute to an injury. To create this understanding, information was drawn from several fields of research including medical equipment, surgical techniques, medicine, engineering, materials science, and ergonomics. Additionally, these fields of research currently do not intersect in a way that a model of material repetitive stress injuries and guidelines can be created easily (or has been developed). This is demonstrated by the body of research and its focus. For example, medical, therapeutic, and pharmacological research is dedicated to (or focuses on) individuals after injury has occurred: surgical procedures, physical therapy regimens, and treatments to speed recovery. Injury detection is focused on after a patient has self-reported an injury, not to screen for risk prior to injury. There remains a need for a model which can be used to generate guidelines to reduce or ameliorate soft tissue injuries from a workplace or other occupational and recreational activities.

SUMMARY

The present disclosure is directed to systems and related methods of generating tendon damage models. Typically, these systems and related methods involve generating guidelines for mitigating or minimizing tendon material repetitive injury.

According to various examples, a method of reducing the potential for repetitive stress injuries to soft tissue in performing a process is disclosed. The method includes obtaining at least one repetitive stress data set related to the soft tissue and to the process; accessing at least first information characterizing a first damage regime and second information characterizing a second damage regime, wherein the first information quantifies a number of repetitions at a given stress for the soft tissue to transition out of the first damage regime, and wherein the second information quantifies a number of repetitions at a given stress for the soft tissue to transition out of the second damage regime; predicting, based on at least the first information, the second information, and the repetitive stress data set, conditions sufficient for damage to the soft tissue; determining, based on at least the predicting, at least one guideline for reducing a risk of a soft tissue material repetitive stress injury; and implementing the at least one guideline in the process.

Various optional features of the above examples include the following. The first damage regime and the second damage regime may each include one of: a No Damage Regime, a Sub-Rupture Damage Regime, or a Tear Propagation Regime. The method may include accessing third information characterizing a third damage regime, wherein the third information quantifies a number of repetitions at a given stress for the soft tissue to transition out of the third damage regime; wherein the first damage regime comprises a No Damage Regime, the second damage regime comprises a Sub-Rupture Damage Regime, and the third damage regime comprises a Tear Propagation Regime. The repetitive stress data set may include a force over a cross sectional area of the soft tissue and at least one of a number of repetitions for, or a duration of, at least one task of the process. The obtaining the at least one repetitive stress data set related to the soft tissue and to the process may include estimating at least one stress distribution in the soft tissue. The at least one guideline may include a limitation on at least one of: a posture of the soft tissue, a number of repetitions of a given movement of the soft tissue, a force applied to the soft tissue, a duration of maintaining a given posture of the soft tissue, a duration of a repetition of a given movement of the soft tissue, or a duration of a given force applied to the soft tissue. The accessing at least first information characterizing a first damage regime and second information characterizing a second damage regime may include obtaining at least one of: ultrasound data, computerized axial tomography (CAT) scan data, magnetic resonance imaging (MRI) scan data, destructive testing data, cadaver material data, animal material data, polymer surrogate material data, molecular dynamic modeling (MDM) data, or publication data. The soft tissue may include a teres minor tendon, an infraspinatus tendon, a supraspinatus tendon, a subscapularis tendon, a deltoid tendons, a biceps tendon, a triceps tendon, a brachioradialis tendon, a supinator tendon, a flexor carpi radialis tendon, a flexor carpi ulnaris tendon, an extensor carpi radialis tendon, an extensor carpi radialis brevis tendon, an iliopsoas tendon, an obturator internus tendon, an adductor longus tendon, an adductor brevis tendon, an adductor magnus tendon, a gluteus maximus tendon, a gluteus medius tendon, a quadriceps tendon, a patellar tendon, a hamstring tendon, a sartorius tendon, a gastrocnemius tendon, an Achilles tendon, a soleus tendon, a tibialis anterior tendon, a peroneus longus tendon, a flexor digitorum longus tendon, an interosseus tendon, a flexor digitorum profundus tendon, an abductor digiti minimi tendon, an opponens pollicis tendon, a flexor pollicis longus tendon, an extensor tendon, an abductor pollicis tendon, a flexor hallucis longus tendon, a flexor digitorum brevis tendon, a lumbrical tendon, an abductor hallucis tendon, a flexor digitorum longus tendon, an abductor digiti minimi tendon, an ocular tendon, a levator palpebrae tendon, a masseter tendon, a temporalis tendon, a trapezius tendon, a sternocleidomastoid tendon, a semispinalis capitis tendon, a splenius capitis tendon, a mylohyoid tendon, a thyrohyoid tendon, a sternohyoid tendon, a rectus abdominis tendon, an external oblique tendon, a transversus abdominis tendon, a latissimus dorsi tendon, or an erector spinae tendon. The method may include individualizing the at least one guideline for a subject by applying one or more demographic variables for the subject to the at least one guideline. The method may include obtaining one or more usage data sets for the soft tissue in a subject; and estimating damage to the soft tissue in the subject by comparing the usage data sets to the at least one guideline.

According to various examples, a computer system for reducing repetitive stress injuries to soft tissue in performing a process is disclosed. The system includes at least one electronic processor that executes instructions to perform operations comprising: obtaining at least one repetitive stress data set related to the soft tissue and to the process; accessing at least first information characterizing a first damage regime and second information characterizing a second damage regime, wherein the first information quantifies a number of repetitions at a given stress for the soft tissue to transition out of the first damage regime, and wherein the second information quantifies a number of repetitions at a given stress for the soft tissue to transition out of the second damage regime; predicting, based on at least the first information, the second information, and the repetitive stress data set, conditions sufficient for damage to the soft tissue; and determining, based on at least the predicting, at least one guideline for reducing a risk of a soft tissue material repetitive stress injury; whereby the at least one guideline is implemented in the process.

Various optional features of the above examples include the following. The first damage regime and the second damage regime may each include one of: a No Damage Regime, a Sub-Rupture Damage Regime, or a Tear Propagation Regime. The operations may further comprise: accessing third information characterizing a third damage regime, wherein the third information quantifies a number of repetitions at a given stress for the soft tissue to transition out of the third damage regime; wherein the first damage regime comprises a No Damage Regime, the second damage regime comprises a Sub-Rupture Damage Regime, and the third damage regime comprises a Tear Propagation Regime. The repetitive stress data set may include a force over a cross sectional area of the soft tissue and at least one of a number of repetitions for, or a duration of, at least one task of the process. The obtaining the at least one repetitive stress data set related to the soft tissue and to the process may include estimating at least one stress distribution in the soft tissue. The at least one guideline may include a limitation on at least one of: a posture of the soft tissue, a number of repetitions of a given movement of the soft tissue, a force applied to the soft tissue, a duration of maintaining a given posture of the soft tissue, a duration of a repetition of a given movement of the soft tissue, or a duration of a given force applied to the soft tissue. The accessing at least first information characterizing a first damage regime and second information characterizing a second damage regime may include obtaining at least one of: ultrasound data, computerized axial tomography (CAT) scan data, magnetic resonance imaging (MRI) scan data, destructive testing data, cadaver material data, animal material data, polymer surrogate material data, molecular dynamic modeling (MDM) data, or publication data. The soft tissue may include a teres minor tendon, an infraspinatus tendon, a supraspinatus tendon, a subscapularis tendon, a deltoid tendons, a biceps tendon, a triceps tendon, a brachioradialis tendon, a supinator tendon, a flexor carpi radialis tendon, a flexor carpi ulnaris tendon, an extensor carpi radialis tendon, an extensor carpi radialis brevis tendon, an iliopsoas tendon, an obturator internus tendon, an adductor longus tendon, an adductor brevis tendon, an adductor magnus tendon, a gluteus maximus tendon, a gluteus medius tendon, a quadriceps tendon, a patellar tendon, a hamstring tendon, a sartorius tendon, a gastrocnemius tendon, an Achilles tendon, a soleus tendon, a tibialis anterior tendon, a peroneus longus tendon, a flexor digitorum longus tendon, an interosseus tendon, a flexor digitorum profundus tendon, an abductor digiti minimi tendon, an opponens pollicis tendon, a flexor pollicis longus tendon, an extensor tendon, an abductor pollicis tendon, a flexor hallucis longus tendon, a flexor digitorum brevis tendon, a lumbrical tendon, an abductor hallucis tendon, a flexor digitorum longus tendon, an abductor digiti minimi tendon, an ocular tendon, a levator palpebrae tendon, a masseter tendon, a temporalis tendon, a trapezius tendon, a sternocleidomastoid tendon, a semispinalis capitis tendon, a splenius capitis tendon, a mylohyoid tendon, a thyrohyoid tendon, a sternohyoid tendon, a rectus abdominis tendon, an external oblique tendon, a transversus abdominis tendon, a latissimus dorsi tendon, or an erector spinae tendon. The soft tissue is not limited to tendons. The soft tissue may also or instead include ligaments, vertebral disks, muscles, skin, etc. For example, using the example of lower back injuries, spinal disks and tendons are both made of soft tissue (e.g., type II collagen vs type I/III). Thus, the model inputs can be updated and different anatomical structures can be imported to extend the operations to other types of soft tissue such as spinal disks. Bone properties can also be incorporated in the definition of the shoulder region. As a result, fractures can be studied elsewhere in the body. Analysis of muscle tissue with fibers in a primary load direction can follow similar methodology to tendons as well. The operations may further include individualizing the at least one guideline for a subject by applying one or more demographic variables for the subject to the at least one guideline. The operations may further include: obtaining one or more usage data sets for the soft tissue in a subject; and estimating damage to the soft tissue in the subject by comparing the usage data sets to the at least one guideline.

In one aspect, the present disclosure provides a method of generating a tendon damage model (e.g., a tendon damage accumulation model, etc.). The method includes generating one or more S-N curves for one or more physical regimes of at least one tendon from one or more S-N curve data sets, wherein a given S-N curve comprises a plot of a magnitude of stress applied to the tendon versus a number of repetitions to failure of the tendon. The method also includes generating one or more repetitive stress data sets that describe the tendon, and combining the S-N curves, or data derived therefrom, with the repetitive stress data sets to predict damage to the tendon under one or more conditions (e.g., physical or tangible representations or information of the tendon damage under a given set of conditions), thereby generating the tendon damage model. It should be noted, however, that the physical mechanism by which damage is accumulated in biological materials, such as collagen-based tendon, is very different from that of traditional crystalline, structural materials, from which the S-N type behavior model was based. The common model for the latter is damage accumulation via dislocation pile-up at glide obstacles in (typically) metallic grains, or crystals. As more cycles are applied, dislocations are generated at discontinuities in the structural material microstructure and gradually pile up against an obstacle, and even though the macroscopic stress is well below the material yield strength, continual cyclic loading will eventually result in a small fissure at the pile-up location. This will then behave as a material defect and eventually grow into a crack. Although prior art approaches have attempted to model fatigue within soft tissue, such attempts produce inaccurate results because they treat soft tissue as if it had the fatigue properties of metal. However, the fatigue and crack mechanism of metals has no true analogue in collagen-based tendons subject to similar cyclic loading, though the S-N type behavior is observed. This is because there are no dislocations accommodating local plastic deformation in tendons. Tendons instead accommodate cyclic loading by localized stretching and kinking of collagen fibers, which can be considered to be a form of micro-damage. Such damage can be repaired by the body by reorganization of the collagen, but it is time-based and subject to healing processes within the body. Hence, an effective model for damage accumulation in tendon structures incorporates: a) a representation of micro-damage accumulation, in advance of a detectable defect (or tear); b) a representation of the healing processes counteracting said micro-damage at a competing rate; c) a representation of the linking up and extension of micro-damage to create a detectable macroscopic defect in the tendon, typically represented as a tear or fissure of the collagen structure and may also be coincident with pain; d) a representation of the extension and growth of this tear or fissure with time (da/dn) if continued cyclic loading is applied above a critical threshold stress intensity, Kc; and, e) a representation of the gross load cycles that result in catastrophic separation or effective failure of the tendon to carry service loads. This latter, e), is the usual mode of S-N fatigue-type data. Model components for each of the above processes will identify four (4) regimes of damage accumulation: 1) no damage; 2) micro-damage (subrupture) accumulation; 3) damage accumulation in the form of a growing tear or fissure, cellular matrix damage or other biological damage; and 4) a state of catastrophic failure or separation of the tendon structure. These model components can be represented mathematically and integrated into a collective model. Such a collective model is also validated by inspection or interrogation methods that can identify the presence and extent of advancing micro-damage and tears.

In another aspect, the present disclosure provides a method of generating a guideline for avoiding tendon material repetitive stress and/or tendon damage accumulation. The method includes generating one or more S-N curves for one or more physical regimes of at least one tendon from one or more S-N curve data sets, wherein a given S-N curve comprises a plot of a magnitude of stress applied to the tendon versus a number of repetitions to reach a damage regime transition for the tendon. The method also includes generating one or more repetitive stress data sets that describe the tendon, and combining the S-N curves, or data derived therefrom, with the repetitive stress data sets to predict damage to the tendon under one or more conditions to produce a tendon damage model. In addition, the method also includes generating at least one guideline for tendon material repetitive stress for the tendon from the tendon damage model, wherein the guideline comprises a posture of the tendon, a number of repetitions of a given movement of the tendon, a force applied to the tendon, a duration of maintaining a given posture of the tendon, a duration of a repetition of a given movement of the tendon, a duration of a given force applied to the tendon, and a combination thereof, thereby generating the tendon damage model, which is used to obtain at least one guideline.

The methods of the present disclosure include various aspects. In some aspects, for example, the methods include combining multiple S-N curves for the physical regimes to produce at least one combined S-N curve. In certain aspects, the methods include applying at least one cumulative damage model when combining the S-N curves, or the data derived therefrom, with the repetitive stress data sets to predict the damage to the tendon under the one or more conditions. In some aspects, the methods include obtaining the S-N curve data sets using one or more data sources comprising medical diagnostic techniques, such as ultrasound data, computerized axial tomography (CAT) scan data, magnetic resonance imaging (MRI) scan data, destructive testing data, cadaver material, animal material, polymer surrogate material, molecular dynamic modeling (MDM) data, publication data, and a combination thereof.

In certain aspects, the tendon comprises a supraspinatus tendon. In some aspects, the tendon comprises a teres minor tendon, an infraspinatus tendon, a supraspinatus tendon, a subscapularis tendon, a deltoid tendons, a biceps tendon, a triceps tendon, a brachioradialis tendon, a supinator tendon, a flexor carpi radialis tendon, a flexor carpi ulnaris tendon, an extensor carpi radialis tendon, an extensor carpi radialis brevis tendon, an iliopsoas tendon, an obturator internus tendon, an adductor longus tendon, an adductor brevis tendon, an adductor magnus tendon, a gluteus maximus tendon, a gluteus medius tendon, a quadriceps tendon, a patellar tendon, a hamstring tendon, a sartorius tendon, a gastrocnemius tendon, an Achilles tendon, a soleus tendon, a tibialis anterior tendon, a peroneus longus tendon, a flexor digitorum longus tendon, an interosseus tendon, a flexor digitorum profundus tendon, an abductor digiti minimi tendon, an opponens pollicis tendon, a flexor pollicis longus tendon, an extensor tendon, an abductor pollicis tendon, a flexor hallucis longus tendon, a flexor digitorum brevis tendon, a lumbrical tendon, an abductor hallucis tendon, a flexor digitorum longus tendon, an abductor digiti minimi tendon, an ocular tendon, a levator palpebrae tendon, a masseter tendon, a temporalis tendon, a trapezius tendon, a sternocleidomastoid tendon, a semispinalis capitis tendon, a splenius capitis tendon, a mylohyoid tendon, a thyrohyoid tendon, a sternohyoid tendon, a rectus abdominis tendon, an external oblique tendon, a transversus abdominis tendon, a latissimus dorsi tendon, an erector spinae tendon, and a combination thereof. In some aspects, the tendon comprises a mammalian tendon. In certain of these aspects, the mammalian tendon comprises a human tendon. In other aspects, the tendon comprises a non-mammalian tendon.

In certain aspects, the methods include combining the S-N curves, or data derived therefrom, and the repetitive stress data sets with healing data to predict damage to the tendon under one or more conditions. In some aspects, the present disclosure provides a method of predicting tendon damage in a subject that includes obtaining one or more usage data sets for at least one tendon in the subject, and comparing the usage data sets to the guideline for tendon material repetitive stress generated by the method, thereby predicting the tendon damage in the subject. In certain aspects, the physical regimes comprise a No Damage Regime, a Sub-Rupture Damage Regime, a crack initiation regime, a fracture regime or curve, and a combination thereof. In some aspects, one or more of the steps are at least partially computer implemented.

In some aspects, the methods include generating at least one guideline for tendon material repetitive stress for the tendon from the tendon damage model, wherein the guideline comprises a posture and/or position of the tendon, a number of repetitions of a given movement of the tendon, a force applied to the tendon, a duration of maintaining a given posture of the tendon, a duration of a repetition of a given movement of the tendon, a duration of a given force applied to the tendon, and a combination thereof. In some of these aspects, the guideline for tendon material repetitive stress comprises one or more recommended use/rest cycles for the tendon under one or more sets of usage conditions.

In certain of these aspects, the methods include validating the guideline for tendon material repetitive stress. In some of these aspects, the methods include individualizing the guideline for a given subject by applying one or more demographic variables for the subject to the guideline. In certain of these aspects, the methods include using task information when generating the guideline. In certain of these aspects, the task information comprises a tool weight and/or a force vector.

In certain aspects, the methods include estimating at least one stress distribution in the tendon to generate the repetitive stress data sets. In some of these aspects, the methods include estimating the stress distribution in the tendon using at least one dimension of the tendon. In certain of these aspects, the dimension comprises at least one cross-sectional area of the tendon. In some of these aspects, the methods include estimating the stress distribution in the tendon using at least one cycle curve that comprises a plot of at least one force applied to the tendon versus the number of repetitions to failure of the tendon. In certain of these aspects, the force is determined at one or more postures of the tendon. In some of these aspects, the methods include determining the force using estimating and/or modeling techniques, such as finite element modeling (FEM) and/or electromyography (EMG). In some of these aspects, the methods include using task information when determining the force applied at the postures of the tendon. In some aspects, the task information comprises a tool weight and/or a force vector.

In other aspects, the present disclosure provides a system, comprising a controller comprising, or capable of accessing, computer readable media comprising non-transitory computer-executable instructions which, when executed by at least one electronic processor perform at least: generating one or more S-N curves for one or more physical regimes of at least one tendon from one or more S-N curve data sets, wherein a given S-N curve comprises a plot of a magnitude of stress applied to the tendon versus a number of repetitions to failure of the tendon, and combining the S-N curves, or data derived therefrom, with one or more repetitive stress data sets to generate a tendon damage model.

In another aspect, the present disclosure provides a computer readable media comprising non-transitory computer-executable instructions which, when executed by at least one electronic processor perform at least: generating one or more S-N curves for one or more physical regimes of at least one tendon from one or more S-N curve data sets, wherein a given S-N curve comprises a plot of a magnitude of stress applied to the tendon versus a number of repetitions to failure of the tendon, and combining the S-N curves, or data derived therefrom, with one or more repetitive stress data sets to generate a tendon damage model.

In some aspects, the instructions of the systems or computer readable media disclosed herein further perform at least: combining multiple S-N curves for the physical regimes to produce at least one combined S-N curve. In certain aspects, the instructions of the systems or computer readable media disclosed herein further perform at least: applying at least one cumulative damage model when combining the S-N curves, or the data derived therefrom, with the repetitive stress data sets to predict the damage to the tendon under the one or more conditions. In some aspects, the instructions of the systems or computer readable media disclosed herein further perform at least: obtaining the S-N curve data sets using one or more data sources comprising medical diagnostic techniques, such as ultrasound data, computerized axial tomography (CAT) scan data, magnetic resonance imaging (MRI) scan data, destructive testing data, cadaver material, animal material, polymer surrogate material, molecular dynamic modeling (MDM) data, publication data, and a combination thereof. In some aspects, the instructions of the systems or computer readable media disclosed herein further perform at least: combining the S-N curves, or data derived therefrom, and the repetitive stress data sets with healing data to predict damage to the tendon under one or more conditions. In certain aspects, the instructions of the systems or computer readable media disclosed herein further perform at least: obtaining one or more usage data sets for at least one tendon in the subject, and comparing the usage data sets to the guideline for tendon material repetitive stress to predict tendon damage in a subject.

In some aspects, the instructions of the systems or computer readable media disclosed herein further perform at least: generating at least one guideline for tendon material repetitive stress for the tendon from the tendon damage model, wherein the guideline comprises a posture of the tendon, a number of repetitions of a given movement of the tendon, a force applied to the tendon, a duration of maintaining a given posture of the tendon, a duration of a repetition of a given movement of the tendon, a duration of a given force applied to the tendon, and a combination thereof. In certain aspects, the instructions of the systems or computer readable media disclosed herein further perform at least: validating the guideline for tendon material repetitive stress. In some of these aspects, the instructions of the systems or computer readable media disclosed herein further perform at least: individualizing the guideline for a given subject by applying one or more demographic variables for the subject to the guideline. In some of these aspects, the instructions of the systems or computer readable media disclosed herein further perform at least: using task information when generating the guideline. In certain of these aspects, the instructions of the systems or computer readable media disclosed herein further perform at least: estimating at least one stress distribution in the tendon to generate the repetitive stress data sets. In some of these aspects, the instructions of the systems or computer readable media disclosed herein further perform at least: estimating the stress distribution in the tendon using at least one dimension of the tendon. In some of these aspects, the instructions of the systems or computer readable media disclosed herein further perform at least: estimating the stress distribution in the tendon using at least one cycle curve comprises a plot of at least one force applied to the tendon versus the number of repetitions to failure of the tendon.

According to various examples, a method for modeling soft tissue is disclosed. The method includes receiving one or more images showing an anatomical geometry of a first subject. The anatomical geometry includes a soft tissue. The method also includes measuring a plurality of parameters of the anatomical geometry of the first subject using one or more sensors attached to the first subject. The method also includes receiving a first set of material properties for the soft tissue of the first subject, a second subject, or both. The method also includes identifying a second set of material properties that characterizes the soft tissue while the first subject performs a task. The second set of material properties is different than the first set of material properties. The method also includes determining a strain on the soft tissue, a stress on the soft tissue, or both based at least partially upon the one or more images, the parameters, the first set of material properties, the second set of material properties, or a combination thereof.

In another implementation, the method includes receiving one or more images showing an anatomical geometry of a subject. The images can be or include magnetic resonance images, computerized tomography images, ultrasound images, or a combination thereof. The anatomical geometry includes soft tissue. The subject is a living mammal. The method also includes measuring a plurality of parameters of the anatomical geometry of the subject. The parameters are measured using one or more sensors attached to the subject. The parameters are measured while the subject performs a task. The parameters include forceful exertion, posture, repetition, duration, vibration, or a combination thereof. The method also includes receiving a first set of material properties for the soft tissue of the subject. The first set of material properties includes in-plane moduli, out-of-plane moduli, Poisson's ratio, or a combination thereof. The method also includes identifying a second set of material properties that characterizes the soft tissue during the task. The second set of material properties is different than the first set of material properties. The second set of material properties includes an isotropic property of the soft tissue, an anisotropic property of the soft tissue, a nonlinear behavior of the soft tissue, an estimated damage state of the soft tissue, or a combination thereof. The method also includes running a finite element model based at least partially upon the one or more images, the parameters, the first set of material properties, the second set of material properties, or a combination thereof. The method also includes determining a strain on the soft tissue, a stress on the soft tissue, or both based at least partially upon the running of the finite element model. The method also includes generating a model that describes the soft tissue based at least partially upon the determined strain, the determined stress, or both.

A system for characterizing a behavior of soft tissue in a mammal is also disclosed. The system includes a plurality of sensors that are configured to be attached to a human subject. The sensors are configured to measure a plurality of parameters while the human subject performs a repetitive task. The parameters include forceful exertion, posture, repetition, duration, vibration, or a combination thereof. The system also includes a computing system configured to perform operations. The operations include receiving one or more images that show an anatomical geometry of the human subject. The images can be or include magnetic resonance images, computerized tomography images, ultrasound images, or a combination thereof. The anatomical geometry includes soft tissue. The operations also include receiving the parameters from the sensors. The operations also include receiving a first set of material properties for the soft tissue of the human subject. The first set of material properties includes in-plane linear moduli, out-of-plane linear moduli, Poisson's ratio, or a combination thereof. The operations also include identifying a second set of material properties that characterizes the soft tissue during the repetitive task. The second set of material properties is different than the first set of material properties. The second set of material properties includes an isotropic property of the soft tissue, an anisotropic property of the soft tissue, a nonlinear behavior of the soft tissue, an estimated damage state of the soft tissue, or a combination thereof. The operations also include running a finite element model based at least partially upon the one or more images, the parameters, the first set of material properties, the second set of material properties, or a combination thereof. The operations also include predicting a strain mode, a stress mode, a vibration mode, and/or a failure mode of the soft tissue based at least partially upon the running of the finite element model. The operations also include generating a model that describes the soft tissue based at least partially upon the strain mode, the stress mode, the vibration mode, the failure mode, or a combination thereof.

DRAWINGS

The above and/or other aspects and advantages will become more apparent and more readily appreciated from the following detailed description of examples, taken in conjunction with the accompanying drawings, in which.

DETAILED DESCRIPTION

Figure 1:
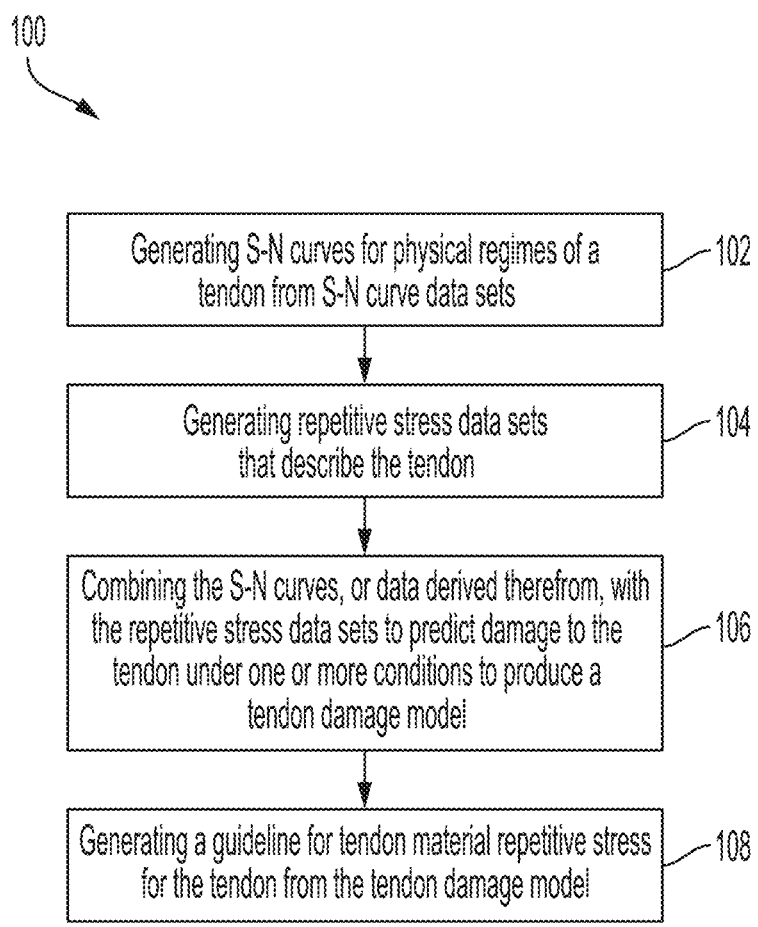
FIG. 1 is a flow chart that schematically depicts exemplary method steps according to some aspects disclosed herein.

Exemplary aspects will now be described more fully with reference to the accompanying drawings. Examples of the disclosure, however, can be embodied in many different forms and should not be construed as being limited to the examples set forth herein. Rather, these examples are provided so that this disclosure will be thorough and complete, and will fully convey the scope to those skilled in the art. In the drawings, some details may be simplified and/or may be drawn to facilitate understanding rather than to maintain strict structural accuracy, detail, and/or scale.

It will be understood that when an element is referred to as being "on," "associated with," "connected to," "electrically connected to," or "coupled to" to another component, it may be directly on, associated with, connected to, electrically connected to, or coupled to the other component or intervening components may be present. In contrast, when a component is referred to as being "directly on," "directly associated with," "directly connected to," "directly electrically connected to," or "directly coupled to" another component, there are no intervening components present. As used herein, the term "and/or" includes any and all combinations of one or more of the associated listed items.

It will be understood that although the terms first, second, etc., may be used herein to describe various elements, components, and/or directions, these elements, components, and/or directions should not be limited by these terms. These terms are only used to distinguish one element, component, and/or direction from another element, component, and/or direction. For example, a first element, component, or direction could be termed a second element, component, or direction without departing from the teachings of examples.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation(s) depicted in the figures.

As used herein, a given "component" and corresponding "component connector" refers to at least two components that are structured or otherwise operable to be joined, operably connected, or otherwise associated with one another. In certain aspects, one component is structured or otherwise operable to be joined, operably connected, or otherwise associated with multiple component connectors. In some aspects, one component connector is structured or otherwise operable to be joined, operably connected, or otherwise associated with multiple components.

As used herein, "subject" refers to an animal, such as a mammalian species (e.g., human) or avian (e.g., bird) species or to non-mammalian species (e.g., fish, mollusks, reptiles, amphibians, etc.). More specifically, a subject can be a vertebrate, e.g., a mammal such as a mouse, a primate, a simian or a human. Animals include farm animals (e.g., production cattle, dairy cattle, poultry, horses, pigs, and the like), sport animals, and companion animals (e.g., pets or support animals). A subject can be a healthy individual, an individual that has or is suspected of having a disease or a predisposition to the disease, or an individual that is in need of therapy or suspected of needing therapy.

The terminology used herein is for the purpose of describing particular examples only and is not intended to be limiting of examples. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which examples belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

While traditional ergonomics practices seek to prevent injuries, it has only or so far been done so at the macro level with epidemiological methods: based on estimated work exposure, create an estimate when will a person self-report an injury based on discomfort level or pain, and create guidelines below that threshold and most injuries are defined by generalized body area: the entire shoulder, knee, or back, but not individual components. Engineering publications starting from the 1990s demonstrated ex vivo tendon materials are subject to strength reduction following repetitive stress, consistent with structural fatigue principles. These works did not report on the utility of this information for creating a model, or preventing or predicting injury. Neither did they explore significant structure and property differences between tendon and non-biological structures, nor the need to identify (or develop) engineered materials that could be used as surrogates for further testing, instead of tendon, which is difficult to obtain and subject to changes and degradation once removed from living tissue. A new approach is needed that ties together multidisciplinary research, fills the gaps, and takes advantage of evolving technology in several fields. Significant advances in computer technology make the creation of a materials model more compelling. Computational material models can simulate fatigue behavior of existing or potential new materials. Ultrasonic interrogation can estimate material acoustic properties of biological material within a living subject, and these can be correlated with certain mechanical properties, such as elastic modulus. Motion tracking technology can be used to observe a person in work and simulate those movements within a digital body. These technologies represent an opportunity to develop a model which can generate guidelines to reduce or ameliorate soft tissue injuries. The model can also take into account individual characteristics to create a model that is personalized. A working model can also be used in reverse: to inform design requirements for building artificial or replacement tendons and how those tendons would perform in a lifetime of movements.

The present disclosure relates to methods, systems, computer readable media and related models for determining and predicting tendon use based, in certain aspects, on materials sciences principles such as force (e.g., at different postures), stress distribution, stress data, and material (e.g., tendon) performance parameters (e.g., healthy state, healing, accumulating damage, and damaged). The present disclosure identifies useful correlations between materials science principles and tendons. In some applications, the predictive model is used in addressing ergonomic issues related to a task to inform and establish guidelines to prevent or otherwise mitigate potential for an injury. Although much of the present disclosure focuses on shoulder injuries and the supraspinatus tendon as one particular example, the methods and related aspects disclosed herein can also be applied to essentially any soft tissue, such as intervertebral (spinal) discs, ligaments, tendons, and tendon system of interest and in biomimicry applications, such as in the design of artificial tendons. An example of how the present disclosure may be applied to any soft tissue is described with respect to FIG. 4 below.

By way of further introduction, using the shoulder for performing work in a workplace is a challenge in extreme work environments. Shoulder injuries also often occur outside of the workplace, e.g., while at home and while participating in sports or other occupational activities. Current guidelines do not provide clear, acceptable limits for shoulder-based work activity in a workplace and they do not account for the interaction of posture, force and repetition, nor the interaction of posture, force, repetition, duration, and vibration. Practitioners who are not able to simply eliminate shoulder movements are faced with degrees of unknown risk. Therefore, robust threshold limit guidelines for shoulder-joint demand are needed that address the complex nature of upper extremity work that includes the interaction of force, repetition and posture and work/rest cycles. Such guidelines are very helpful to industrial engineers and ergonomists, but can also be helpful for physicians, physical therapists, sports medicine practitioners, and sports coaches, among others.

It has been well documented that shoulder disorders are common and frequent in extreme workplaces such as heavy manufacturing, welding, fisheries, meat processing, heavy machining, auto repair and painting. U.S. Bureau of Labor Statistics 2013 data show that cumulative trauma injuries to the shoulder accounted for 15% of all workplace musculoskeletal injuries, exceeded only by lower back and general back injuries; however, shoulder injuries tended to be more severe, resulting in more time loss.

Shoulder mechanisms permit the placement, functioning, and control of the hand, the most useful part of the human body for manual labor or tool-intensive assembly. Hands, and therefore arms and shoulders, move to weld, paint, drill, cut, gut fish, or handle materials. The tool, hand, and shoulder system are often positioned overhead or in hard to reach places. The shoulder complex must support the weight of the arm, any tools being held to perform work, and force applied. Most manual work involving tools include tasks to be repeated many times during the course of a work period.

A neutral shoulder posture is the upper arm straight and hanging alongside the body. Every time a shoulder is out of its neutral position, tendons are placed under tensile force, creating stress within the tendon. Each time the shoulder moves away from neutral position, force and repetition occur, exposing the tendon to cumulative fatigue damage.

Studies linking shoulder pain or rotator cuff injuries to workplace factors identify overhead work (defined as elbows above shoulders), applied force, repetitive motion, and physical loads as significant contributors. However, the quality of these studies varies, and evidence did not consistently demonstrate a significant dose-response relationship although since then, two studies have related upper arms elevated above 90° with specific outcomes of tendon damage detected in MRI or impingement surgery. A review specifically focused on evidence of workplace factors in rotator cuff tendon disorder outcomes and found research lacking.

Even for studies with a specific outcome, the exposure assessments in these research papers were too gross, and classification of outcome still not specific enough to establish a strong quantitative association between 'dose and response' or 'exposure and risk'. As a result, current published guidelines for shoulder-demand injury risk are insufficient for use in occupational ergonomics injury prevention programs. These guidelines simply recommend reduction or elimination of overhead or extended shoulder postures; they do not specify to what degree reduction is needed to significantly impact injury rates.

While eliminating repetitive, awkward or taxing shoulder use is infeasible in some industries, it could be ameliorated. Without available risk thresholds, the question persists as to what degree these risk factors should be reduced to prevent injury. The question is further complicated because this type of work can involve many repetitive motions (painting) and/or forces (drilling) and/or loads (welding). Any useful guideline should also include risk factor interaction and work/rest cycles.

Given the inability of establishing causality with epidemiological data alone, an alternative approach is needed. The models and related aspects disclosed herein bridge many of the gaps that traditional epidemiological studies have not been able to close and instead uses a fatigue model of cumulative damage to predict and prevent injuries in certain aspects.

The term "fatigue" is used throughout this disclosure in its mechanical sense—structural degradation from repeated forces—rather than physiological fatigue, which is the inability to perform activity because muscle contractile forces are reduced. The term "resultant force" is used to indicate the tensile force on the tendon caused by the tool weight, body segment posture, and force applied to the tool by the worker. More generally, "resultant force" refers to a combination of the forces acting on soft tissue during work, including posture (e.g., shoulder position), vibration, tool weight, force vector applied at the hand, arm weight, etc. Tensile force is relevant to shoulders, but other soft tissue, such as intervertebral discs, can experience compressive force. Other types of soft tissue can experience both compressive and tensile forces.

When people are engaged in physical activity, the effects of repeated stress on soft tissues result in small fissures often referred to as microtrauma or subruptures. Subruptures themselves are not harmful to the body because the body will repair itself to become stronger given a sufficient recovery period; this is the underlying benefit of exercise. With insufficient recovery period, the tendon becomes damaged and eventually an injury will occur. Sufficient recovery period for tendon use (or overuse) was previously undetermined, unknown, or undefined.

Robust guidelines are needed that provide clear, acceptable limits and rest cycles for shoulder-based work activity, which account for the interactions between posture, force, duration, vibration, and repetition.

The models for supraspinatus tendon fatigue and repair periods disclosed herein are advantageous for heavy industry, especially where overhead work, repetition, and force exist, and for sports. Tendons behave like materials, with predictable fatigue failure at given stress levels and cycles, but they are also able to self-repair.

The approaches presented herein draw, for example, on principles from materials science and medicine to propose such models. The models can be used to set exposure limits and create usable work/rest cycles to predict and reduce or ameliorate shoulder overuse injuries, leading to a significant change in current approaches to mitigating and reducing shoulder injuries.

In certain aspects, the models disclosed herein do not include all aspects of tendon behavior. The prevalence of occupational shoulder injuries outweighs the limited amount of research currently taking place and much opportunity exists for collaborative research between such diverse groups as aerospace engineers, fatigue experts, orthopedic surgeons, and industrial ergonomists, with potentially immense benefits for worker health.

The models disclosed herein can be used to, for example, redesign work practices exceeding reasonable tendon strain or stress thresholds, create work-rest cycles based on collagen damage and repair rates, identify individuals for whom the model is not conservative, and implement strength training to improve tendon material properties.

Note that the disclosed techniques are not limited to tendons. As set forth herein, an example is presented by way of illustration rather than limitation in reference to shoulder tendons. However, examples are not so limited. Other types of soft tissue, such as intervertebral (spinal) discs and ligaments are amenable to analysis and injury amelioration using examples disclosed herein.

Figure 2:
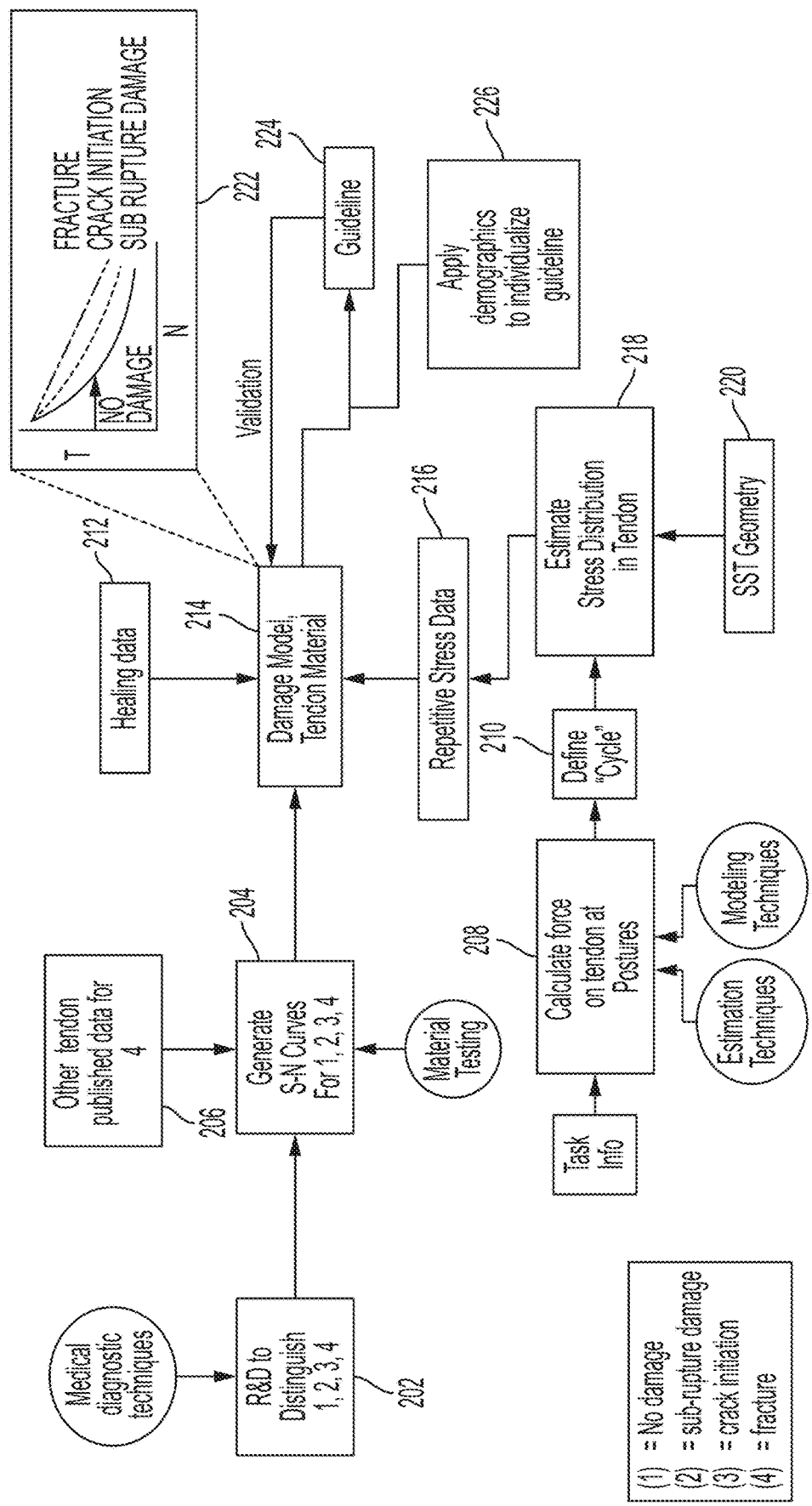
FIG. 2 is a schematic diagram that depicts exemplary method steps according to some aspects disclosed herein.
Figure 3:
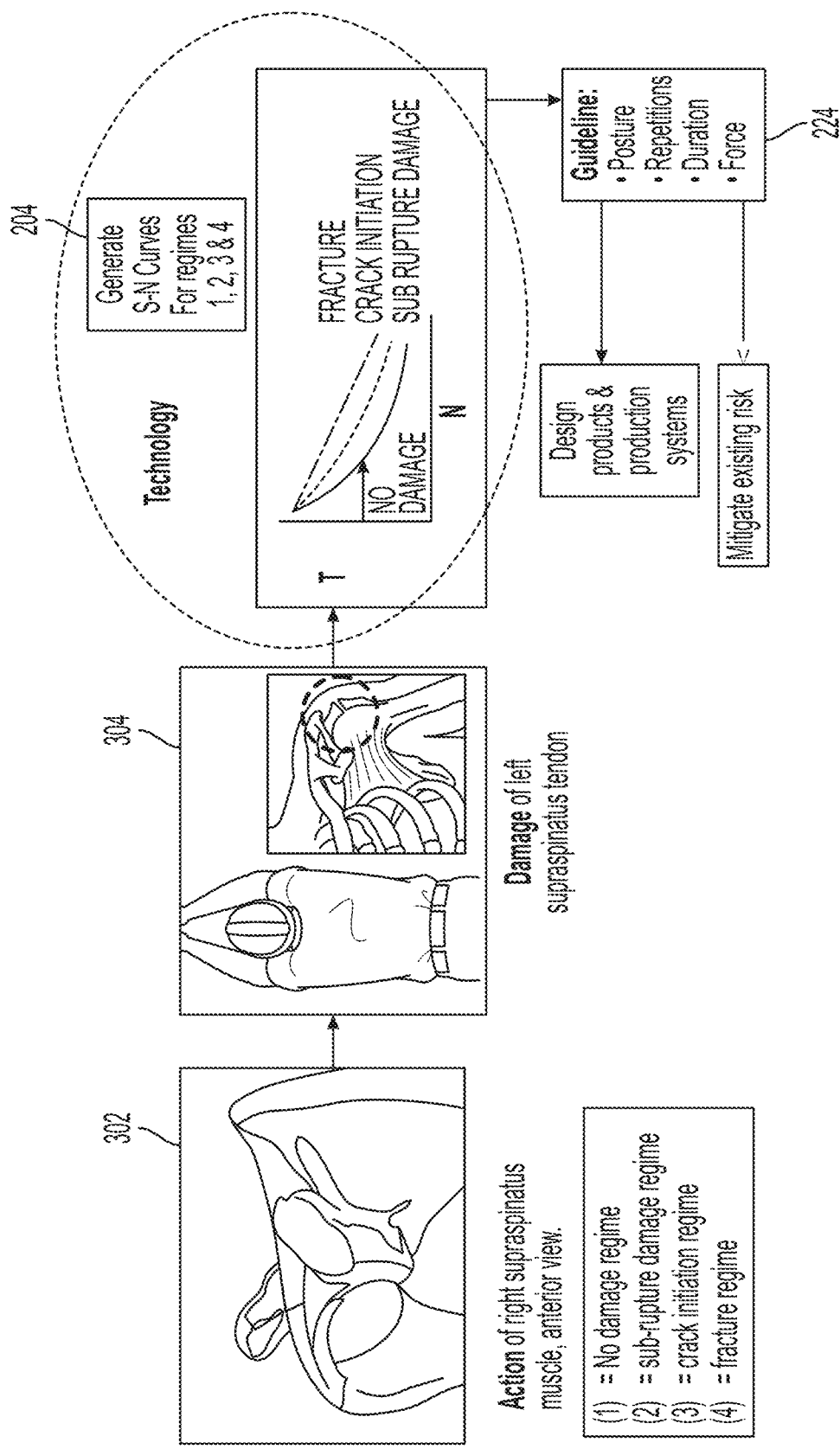
FIG. 3 is a schematic diagram that depicts exemplary method steps according to some aspects disclosed herein.

The present disclosure provides assorted methods of generating a soft tissue damage model and of generating guidelines for soft tissue material repetitive stress. As mentioned above, portions of the description may focus on a tendon; however, it will be appreciated that this is merely one exemplary type of soft tissue, and the methods disclosed herein are equally applicable to other types of soft tissue (e.g., intervertebral (spinal) discs, ligaments, etc.). Certain aspects of these methods are schematically shown in FIGS. 1-3. As shown, method 100 includes generating one or more S-N curves for one or more physical regimes of soft tissue (e.g., a tendon) from one or more S-N curve data sets (step 102, 204). A given S-N curve typically comprises a plot of a magnitude of stress applied to the tendon versus a number of repetitions to failure of the tendon. Model components for each of the above processes will identify four (4) regimes of damage accumulation: 1) no damage; 2) micro-damage (subrupture) accumulation; 3) damage accumulation in the form of a growing tear or fissure, cellular matrix damage or other biological damage; and 4) a state of catastrophic failure or separation of the tendon structure. Method 100 also includes generating one or more repetitive stress data sets that describe the tendon (step 104, 216). Method 100 also includes combining the S-N curves (222), or data derived therefrom, with the repetitive stress data sets (216) to predict damage to the tendon under one or more conditions to generate a tendon damage model (step 106, 216) (e.g., physical or tangible representations or information of the tendon damage under a given set of conditions). In certain aspects, method 100 also typically includes generating at least one guideline for tendon material repetitive stress for the tendon from the tendon damage model (step 108, 224). As used herein, the term "guideline" refers to a recommended set of evidence-based maximum acceptable limits, in terms of force (e.g., vibration, tool weight, force vector applied at the hand, arm weight, etc.), posture, position, frequency, duration and/or recovery, intended to safeguard human tissue material from the risk of injury due to tendon damage during human activity such as manufacturing or other processes. In some aspects, the guideline comprises a posture of the tendon, a number of repetitions of a given movement of the tendon, a force applied to the tendon, a duration of maintaining a given posture of the tendon, a duration of a repetition of a given movement of the tendon, a duration of a given force applied to the tendon, and a combination thereof. As also shown, the methods also include evaluating the action of a given muscle (302) and damage of a given tendon (304) in certain aspects.

The methods of the present disclosure include various aspects. In some aspects, for example, the methods include combining multiple S-N curves for the physical regimes to produce a combined S-N curve (222). In certain aspects, the methods include applying a cumulative damage model when combining the S-N curves (204), or the data derived therefrom, with the repetitive stress data sets (216) to predict the damage to the tendon under one or more conditions. In some aspects, the methods include obtaining the S-N curve data sets using one or more data sources comprising medical diagnostic techniques, such as ultrasound data, computerized axial tomography (CAT) scan data, magnetic resonance imaging (MRI) scan data, destructive testing data, cadaver material, animal material, polymer surrogate material, molecular dynamic modeling (MDM) data, publication data, and a combination thereof (202, 204, 206).

Essentially any tendon can be evaluated as part of the methods disclosed herein. Some exemplary tendons that are optionally used, include a teres minor tendon, an infraspinatus tendon, a supraspinatus tendon, a subscapularis tendon, a deltoid tendons, a biceps tendon, a triceps tendon, a brachioradialis tendon, a supinator tendon, a flexor carpi radialis tendon, a flexor carpi ulnaris tendon, an extensor carpi radialis tendon, an extensor carpi radialis brevis tendon, an iliopsoas tendon, an obturator internus tendon, an adductor longus tendon, an adductor brevis tendon, an adductor magnus tendon, a gluteus maximus tendon, a gluteus medius tendon, a quadriceps tendon, a patellar tendon, a hamstring tendon, a sartorius tendon, a gastrocnemius tendon, an Achilles tendon, a soleus tendon, a tibialis anterior tendon, a peroneus longus tendon, a flexor digitorum longus tendon, an interosseus tendon, a flexor digitorum profundus tendon, an abductor digiti minimi tendon, an opponens pollicis tendon, a flexor pollicis longus tendon, an extensor tendon, an abductor pollicis tendon, a flexor hallucis longus tendon, a flexor digitorum brevis tendon, a lumbrical tendon, an abductor hallucis tendon, a flexor digitorum longus tendon, an abductor digiti minimi tendon, an ocular tendon, a levator palpebrae tendon, a masseter tendon, a temporalis tendon, a trapezius tendon, a sternocleidomastoid tendon, a semispinalis capitis tendon, a splenius capitis tendon, a mylohyoid tendon, a thyrohyoid tendon, a sternohyoid tendon, a rectus abdominis tendon, an external oblique tendon, a transversus abdominis tendon, a latissimus dorsi tendon, an erector spinae tendon, and a combination thereof. In some aspects, the tendon comprises a mammalian tendon. In certain of these aspects, the mammalian tendon comprises a human tendon.

In certain aspects, the methods include combining the S-N curves, or data derived therefrom, and the repetitive stress data sets with healing data to predict damage to the tendon under one or more conditions (212). In some aspects, the present disclosure provides a method of predicting (e.g., forecasting) tendon damage in a subject that includes obtaining one or more usage data sets for at least one tendon in the subject, and comparing the usage data sets to the guideline for tendon material repetitive stress generated by the method, thereby predicting the tendon damage in the subject. In certain aspects, the physical regimes comprise a No Damage Regime, a Sub-Rupture Damage Regime, a crack initiation regime, a fracture regime or curve, and a combination thereof. In some aspects, one or more of the steps are at least partially computer implemented. Systems and related computer readable media are described further herein.

In some aspects, the methods include generating at least one guideline (224) for tendon material repetitive stress for the tendon from the tendon damage model (214) in which the guideline comprises a posture of the tendon, a number of repetitions of a given movement of the tendon, a force applied to the tendon, a duration of maintaining a given posture of the tendon, a duration of a repetition of a given movement of the tendon, a duration of a given force applied to the tendon, and a combination thereof. In some of these aspects, the guideline for tendon material repetitive stress comprises one or more recommended use/rest cycles for the tendon under one or more sets of usage conditions. Typically, the methods include validating the guideline for tendon material repetitive stress. In some of these aspects, the methods include individualizing the guideline for a given subject by applying one or more demographic variables for the subject to the guideline (226). In certain of these aspects, the methods include using task information when generating the guideline (228). In certain of these aspects, the task information comprises a tool weight and/or a force vector.

In certain aspects, the methods include estimating at least one stress distribution in the tendon to generate the repetitive stress data sets (218). In some of these aspects, the methods include estimating the stress distribution in the tendon using at least one dimension of the tendon (220). In certain of these aspects, the dimension comprises at least one cross-sectional area of the tendon. In some of these aspects, the methods include estimating the stress distribution in the tendon using at least one cycle curve that comprises a plot of at least one force applied to the tendon versus the number of repetitions to failure of the tendon (210). In certain of these aspects, the force is determined at one or more postures of the tendon (208). In some of these aspects, the methods include determining the force using an estimation and/or modeling technique, such as finite element modeling (FEM) and/or electromyography (EMG). In some of these aspects, the methods include using task information when determining the force applied at the postures of the tendon. In some aspects, the task information comprises a tool weight and/or a force vector.

In some aspects, the process of combining S-N curves involves cumulative damage modeling around multiple curves and healing. To illustrate, an example might include a repetitive stress data set (this set might correspond to the exposure that a subject might accrue during the course of one task, for example) that comprises:

Task A Force: 150N Repetitions: 50
Task B Force: 100N Repetitions: 500
Task C Force: 50N Repetitions: 5000

The Repetition numbers are derived from observing or sampling the task in certain aspects. The Stress numbers are derived by the digital model of a subject's hand/arm/limb position while performing the task, plus any load the subject is carrying in some aspects. The output would be force (N). Stress is force divided by cross sectional area of the tendon (e.g., an SST Geometry model), which is 50 mm$^2$ in this example. This creates Task A Stress=3 MPa, Task B Stress=2 MPa, and Task C Stress=1 MPa. In this illustration, some information is also available about the S-N curve for where no damage occurs and that the No Damage Regime ends (and subrupture starts) at 1000 cycles at 4 MPa (this is one point along the curve).

All of these numbers are combined to ascertain the amount of damage to the tendon under consideration. In some aspects, Miner's Rule is used as part of this process. In Miner's rule, if 1 is exceeded, that means the S-N curve selected to compare is exceeded. In this case, since the No Damage Regime is selected, exceeding 1 means that the No Damage Regime no longer applies and instead, one of the other regimes does apply.

These tasks are combined with the No Damage Regime limit and (3 MPa*50+2 MPA*500+1 MPa*5000)/(4 MPa*1000)=1.53 is obtained. This means that the No Damage Regime is exceeded since it is >1. Also, if a given guideline specifies that no damage at all is desired, then the guideline has been exceeded. Thus, the next regime (e.g., subrupture) would need to be calculated to and maybe the next one after, if >1, and so on up to the Fracture regime. In some aspects, healing data is also applied if multiple tasks are combined with rest periods in between (e.g., a percentage reduction in exposures, moving to a lower point on the curve, etc.).

The calculations presented above in this illustration provide a point solution (just one number and one answer) for one iteration. For better model fidelity, this iteration could be run a number of times, sampling from distributions of, for example, SST geometries, the digital model for force on tendon, and optionally some variation in the repetitions. For example, this can be a model run multiple times with slightly different probabilistic inputs similar to a Monte Carlo simulation. This provides an output of the risk with some boundaries or bands around it (e.g., a 95% confidence interval, etc.). Optionally, other variables, such as demographics are also added to the model.

Figure 4:
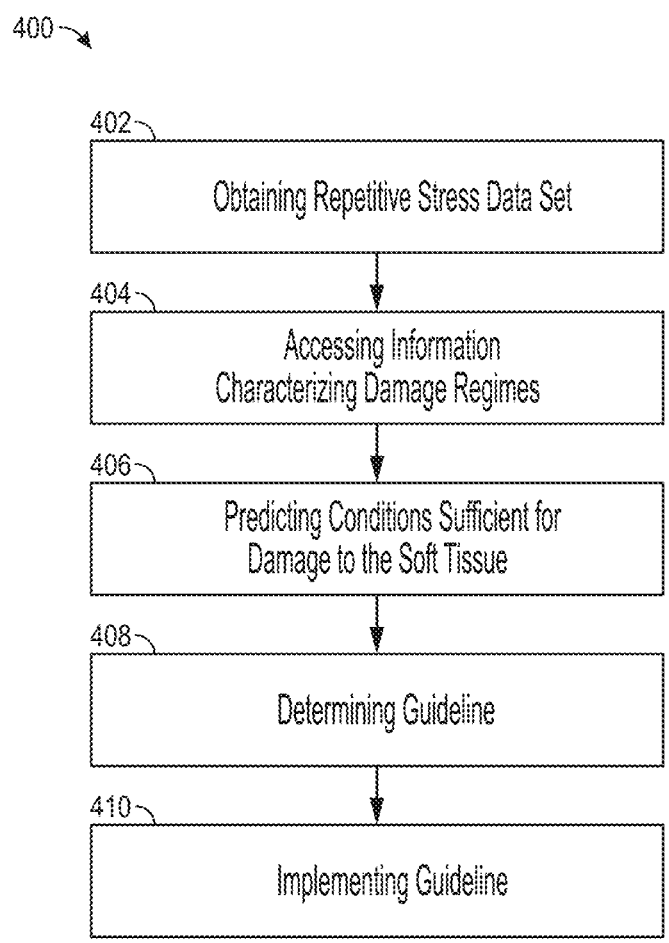
FIG. 4 is a flow chart depicting a method of providing at least one guideline for reducing a risk of a repetitive stress injury to a tendon according to various examples.

FIG. 4 is a flow chart depicting a method 400 of reducing (e.g., ameliorating) repetitive stress injuries to soft tissue in performing a process according to various examples. Method 400 utilizes material science properties of such soft tissue to determine guidelines that, when implemented as described presently in reference to method 400, reduce the potential for injuries to those performing the process. Method 400 can be partially implemented using system 1200, as shown and described below in reference to FIG. 5, for example. Method 400 further includes extra-computer actions that provide improvements in the field of industrial hygiene. Such actions include, for example, obtaining a repetitive stress data set related to the soft tissue and to the process (e.g., a description of force per area of the soft tissue and a number of repetitions) and implementing the guidelines to reduce the potential for repetitive stress injuries to an individual in a process. Method 400 focuses on a tendon as one example of soft tissue; however, as mentioned above, method 400 may also or instead be used to reduce (e.g., ameliorate) repetitive stress injuries to other types of soft tissue (e.g., intervertebral (spinal) discs, ligaments, etc.).

Method 400 can be used to ameliorate repetitive stress injuries of workers performing a part of a manufacturing process; however, this is merely one example, and method 400 can also be used outside of the workplace, as described below. Each worker can have one or more tasks that form part of the manufacturing process, e.g., on an assembly line. The tasks for each worker can be modified by the one or more guidelines produced by method 400. Alternately, method 400 can be used to ameliorate repetitive stress injuries of an athlete executing a training program, for example. The athlete can have one or more exercises that form part of the training program. The exercises can be modified by the one or more guidelines produced by method 400. In general, method 400 can be practiced to ameliorate repetitive stress injuries in any type of process that includes repetitive movements by a person, not limited to manufacturing or athletic processes.

Method 400 can be used to ameliorate injuries to any of a variety of soft tissues. According to some examples, method 400 can be used to ameliorate injuries to tendons or tendon complexes. Examples of such tendons and tendon complexes are presented above in reference to FIGS. 1-3. Alternately, method 400 can be used to ameliorate injuries to connective tissue or musculoskeletal soft tissue. In general, non-limiting examples of soft tissues for which examples can be implemented include tendons, tendon complexes, intervertebral (spinal) discs, and ligaments.

For example, using the example of lower back injuries, spinal disks and tendons are both made of soft tissue (e.g., type II collagen vs type I/III). Thus, the model inputs can be updated in the method 400, and/or different anatomical structures can be imported into the method 400, to extend the method 400 to other types of soft tissue such as spinal disks. Bone properties can also be incorporated in the definition of the shoulder region. As a result, fractures can be studied elsewhere in the body. Analysis of muscle tissue with fibers in a primary load direction can follow similar methodology to tendons as well.

At 402, method 400 includes obtaining at least one repetitive stress data set related to the soft tissue (e.g., tendon, ligament, intervertebral (spinal) discs, etc.) and to the process. The repetitive stress data sets can be in the form of computer files, e.g., in tab-delimited or comma-separated value (CSV) format. The repetitive stress data sets can be obtained by being read from persistent electronic storage by a computer, or by the data being entered into file format and stored in the computer, by way of non-limiting examples.

According to some examples, each repetitive stress data set can represent the exposure that a subject might accrue over the course of completing one task that forms part of the overall process. The exposure can be in the form of a number of repetitions and a force on the soft tissue per repetition. The force can be expressed in Newtons (N) for example. Alternately, each repetitive stress data set can be in the form of a number of repetitions and a stress on the soft tissue per repetitions. The stress can be resultant stress, including stress due to posture (e.g., shoulder position), vibration, tool weight, force vector applied at the hand, arm weight, etc. The stress can be expressed in Megapascals (MPa), for example.

Each repetitive stress data set can further include a description of a movement for each repetition, e.g., in narrative form. Multiple repetitive stress data sets can account for multiple types of movements. Method 400 can obtain the repetitive stress data set(s) by acquiring them in computer readable form (e.g., by user entry) and providing them to a computer program that performs the actions of, e.g., blocks 402, 404, 406, and at least part of 408.

At 404, method 400 includes accessing information characterizing at least two damage regimes. The information can be in the form of computer files, e.g., as pairs for values in tab-delimited or comma-separated value (CSV) format. The information can be accessed by being read from persistent electronic storage by a computer, or by the information being received and stored in the computer, by way of non-limiting examples.

According to various examples, method 400 can access first information characterizing a first damage regime and second information characterizing a second damage regime. According to various examples, method 400 can further access third information characterizing a third damage regime. Each information can quantify a number of repetitions at a given stress for the soft tissue to transition out of the respective damage regime. For example, the first information can quantify a number of repetitions per given stress for the soft tissue to transition out of the first damage regime; the second information can quantify a number of repetitions per given stress for the soft tissue to transition out of the second damage regime, and, for examples that include a third damage regime, the third information can quantify a number of repetitions per given stress for the soft tissue to transition out of the third damage regime.

Each information can be in the form of a curve quantifying a number of repetitions at a given stress for the soft tissue to transition out of the respective damage regime, e.g., with stress as an independent variable and repetitions as a dependent variable. For example, each information can be in the form of an S-N curve, as described herein, according to various examples. When stored in a computer, such information can be in the form of a set of ordered pairs (S, R), where S represents stress and R represents a number of repetitions to transition out of the respective regime.

According to various examples, the first damage regime can be a No Damage Regime, the second damage regime can be a Sub-Rupture Damage Regime, and, for examples that include it, the third damage regime can be a Tear Propagation Regime. (Note that any combination of two or more damage regimes can be used according to various examples, not limited to those explicitly set forth presently.) The No Damage Regime can represent a situation in which micro-damage (e.g., sub-ruptures) occur in the soft tissue at substantially the same rate as they are healed. Transition out of the No Damage Regime can represent sub-rupture accumulation at a rate faster than the healing rate for the respective soft tissue. The sub-rupture regime can represent a situation where the micro-damage (e.g., sub-rupture damage) accumulates, but no macroscopic tear has yet formed. Transition out of the sub-rupture regime can represent that a macroscopic tear has formed. The Tear Propagation Regime can represent a situation where a tear has formed and is propagating through the soft tissue. Transition out of the Tear Propagation Regime can represent that the soft tissue has fully ruptured.

Note that examples that incorporate either or both of the No Damage Regime and the sub-rupture regime can predict damage to subject soft tissue prior to the subject realizing that damage has occurred. For example, soft tissue within these regimes can be damaged, but cause no pain or discomfort to the subject.

At 406, method 400 includes predicting, based on at least the information characterizing the damage regimes and the repetitive stress data set, conditions sufficient for damage to the soft tissue. The damage can be any of: the soft tissue accumulating micro-damage at a rate faster than the healing rate of the soft tissue (e.g., a transition out of the first regime), the soft tissue experiencing a macroscopic tear (e.g., a transition out of the second regime), or the soft tissue experiencing a full rupture (e.g., a transition out of the third regime).

The prediction/forecasting can utilize material science properties of the soft tissue to determine such conditions. According to some examples, the prediction can be performed as follows. First, if not already in terms of stress, the force data in the repetitive stress data set can be converted to units of stress. For example, the repetitive stress data set can be in terms of force on the soft tissue per repetition. By dividing such force by the cross-sectional area of the soft tissue, the repetitive stress data set is converted into units of stress per repetition (and/or per repetition). The system can store soft tissue cross sectional area data to that end. The soft tissue cross sectional area data can include average cross-sectional areas for various soft tissue types, specific cross-sectional areas per demographic combination (e.g., sex, age, gender), or a combination of such data. Second, the repetitive stress data set is compared to the information characterizing the damage regimes. For example, for a repetitive stress data set that represents R repetitions at a stress level of S, that stress level S can be considered an independent variable in the information representing the current damage regime of the soft tissue, and the corresponding dependent variable R' in terms of a number of repetitions for transition out of the damage regime can be identified. Third, the number of repetitions R' of the identified dependent variable is compared with the number R of repetitions set forth in the repetitive stress data set. If the former is greater than the latter, then the soft tissue is predicted to remain in its current damage regime, and therefore no additional damage is predicted. If, however, the former is less than or equal to the latter, then the soft tissue is predicted to transition out of the respective damage regime. In that case, the soft tissue is predicted to undergo damage. Thus, the soft tissue is predicted to undergo damage when the number of repetitions R set forth in the repetitive stress data set for stress level S meets or exceeds the number of repetitions R' corresponding to S per the information characterizing the current damage regime for transition out of the current damage regime.

This process can be extended to include multiple repetitive stress data set. For example, the products of the repetitions and stress levels from the various repetitive set data sets can be summed. This sum can be compared to the product of a stress level and number of repetitions from the information characterizing the current damage regime. If the sum is greater, then the soft tissue is predicted to undergo damage. Otherwise, the soft tissue is predicted to remain in the current damage regime. Note that Miner's Rule, as described in the example above in reference to FIGS. 1-3, can be employed for this comparison.

At 408, method 400 includes determining, based on at least the predicting, at least one guideline for reducing a risk of a soft tissue material repetitive stress injury. In general, the guideline can reduce a number of repetitions and/or an amount of stress corresponding to actions in one or more of the repetitive stress data sets. Such parameters can be reduced until the calculations described above in reference to block 406 predict no damage. The parameters so reduced can form all or part of a guideline.

In general, the guideline can reduce the stress on the soft tissue by reducing the force on the soft tissue in any of a number of ways. The force on the soft tissue can be a resultant force on the soft tissue, the force being the result of posture (or position), weight (e.g., of the arm and/or holding an object such as a tool), applied force vector (e.g., pushing at the hand), vibration (from holding a vibrating object such as a hand tool), etc. According to some examples, the force is reduced by placing a limitation on any of the above parameters.

The force on the soft tissue can alternately, or in addition, be reduced placing a limitation on the position and/or posture of the subject's body or portion thereof, thus affecting a position and/or posture of the soft tissue. According to various examples, the guideline can include a limitation on at least one of a position of the soft tissue, and/or a posture of the soft tissue.

Here, "position" can refer to quantitative characterization of the subject's body or part thereof. For example, a position can be defined using measurement equipment, with units like length, angle, or x-y-z coordinates. For example, a tendon position can be defined at coordinates (0 cm, 5 cm, 1 cm), where origin (0 cm, 0 cm, 0 cm) is where the tendon attaches to the humerus, and the coordinates correspond to positions in the following planes as follows: x=saggital, y=transverse, and z=coronal. A position of a subject (or a portion of the subject's body) can be determined by attaching a motion tracking system to the subject according to various examples.

"Posture" can refer to qualitative characterizations of the subject's body or part thereof. A posture can be defined in terms of relative positions of identified landmarks. For example, a particular posture referred to as "overhead work" can be defined as the situation when the subject's elbow is above the subject's shoulder. In general, a posture can define a body position in a qualitative way, such that it can be observed and compared to another observation or position. A position of a subject (or a portion of the subject's body) can be determined by observational study by an ergonomist or industrial engineer according to various examples.

Alternately, or in addition, the force on the soft tissue can be reduced placing a limitation on a temporal duration of a movement, position, or posture. That is, the guideline can place a limitation on any, or a combination, of: a duration of maintaining a given posture of the soft tissue, a duration of maintaining a given position of the soft tissue, a duration of a repetition of a given movement of the soft tissue, and/or a duration of a given force applied to the soft tissue.

According to some examples, the guidelines can include imposed rest periods. Such examples can utilize a representation of the healing processes that counteract micro-damage or macro-damage. The rest periods can represent sufficient time for such healing processes to counteract any accumulated damage.

The guidelines can be output in any of a variety of forms. According to some examples, the guidelines are output in narrative form using pre-generated narrative templates. For example, if the computations indicate that the number of repetitions should be reduced from 1000 to 725, the guideline can populate these numbers into a template that reads in part, "The number of repetitions for action X should be reduced from Y to Z," where X, is replaced with a description of the action, Y is replaced by 1000, and Z is replaced by 725. The formatted guidelines can be output by displaying on a computer monitor, by email, or by any other techniques that provide the information to a person or process.

At 410, method 400 includes implementing the guideline(s) in the process. To do so, method 400 can include providing the guidelines to workers on an assembly line, for examples in which the process is a manufacturing process. The workers can then alter their tasks accordingly. For examples in which the process is an athletic training process, the guidelines can be provided to the trainer, who alters the athlete's training plan accordingly. Further, the guidelines can be used to design production systems, products, work tasks, training plans, etc.

The system and method disclosed herein can generate a model that uses material properties to characterize the behavior of living mammalian soft tissue (e.g., tendons, discs, etc.) subjected to different loading conditions. The soft tissue can be modeled in response to a number of different loading conditions to characterize damage to the soft tissue during overuse situations to reduce injury potential.

The model can be or include a (e.g., single) finite element model (FEM) that determines or predicts material fatigue of the soft tissue. Instead of or in addition to mammals, the model can also or instead be applied to other species, such as reptiles, amphibians, etc. In one example, the soft tissue can be or include the supraspinatus tendon (SST) in the shoulder. Instead of or in addition to soft tissue, the model can also or instead be applied to connective tissue, musculoskeletal tissue, vertebral discs, etc.

As described in greater detail below, the model can receive input data that is subject to different loading conditions. In one example, the input data can be or include one or more (e.g., five) established ergonomic risk factors: forceful exertion, posture, repetition, duration, and vibration. The model can demonstrate a correlation between simultaneous exposure to these risk factors. A relationship between simultaneous exposure to the ergonomic risk factors is demonstrated herein, thus proving that the interaction of risk factors results in a combined effect that can lead to injury with definite multipliers.

The input data can also or instead include the (linear and/or non-linear) modulus of elasticity of the soft tissue, the strain on the soft tissue, the cross-sectional area of the soft tissue, the percentage of the soft tissue that is healthy, the percentage of the soft tissue that is injured/damaged, or a combination thereof. The input data can also or instead include the 3D anatomical geometry (e.g., of the shoulder), the load transfer path between tissue and bone across one or more joints, the external (e.g., task-related) boundary conditions (e.g., shoulder position or posture), the internal (e.g., anatomy-related) boundary conditions, or a combination thereof. The data can also or instead include the entire system of parameterized and combined interactions, as opposed to an over-generalized task guidance based on empirical studies. In contrast, traditional ergonomic approaches rely on empirical data sets that are focused on the resultant injury rather than modeling initiation of damage based on material behavior on a constituent level.

The model can output one or more fatigue S-N curves. The model can also or instead output an assessment of one or more (e.g., four) regimes of tissue damage: no damage, sub-rupture, partial damage, full damage. The model can also or instead output a comparison of various changes to work procedures and tools (e.g., evaluate reduced range-of-motion, power tools of different weights and vibration frequencies, introduction of ergonomic assist devices, etc.), which can lead to optimized task design guidance and/or recommended work intervals for a given task.

In one implementation, the fidelity of the model can be increased by incorporating nonlinear behavior and introducing complex loading and vibration/fatigue cycling of the soft tissue. This model can validate that finite element modeling is a viable approach to assess healthy and partially damaged tissue, describing fatigue failure properties of a soft tissue, such as a tendon material during overuse.

Vibration effects can be characterized (e.g., while holding a vibrating tool) from the hand through the body and into the soft tissue (e.g., tendon). Characterizing soft tissue material behavior by capturing the viscoelastic behavior across systems, and characterizing the effects of hand/arm/limb (and other parts) vibration, can highlight accelerating material fatigue throughout the soft tissue geometry and accelerating injury.

Figure 5:
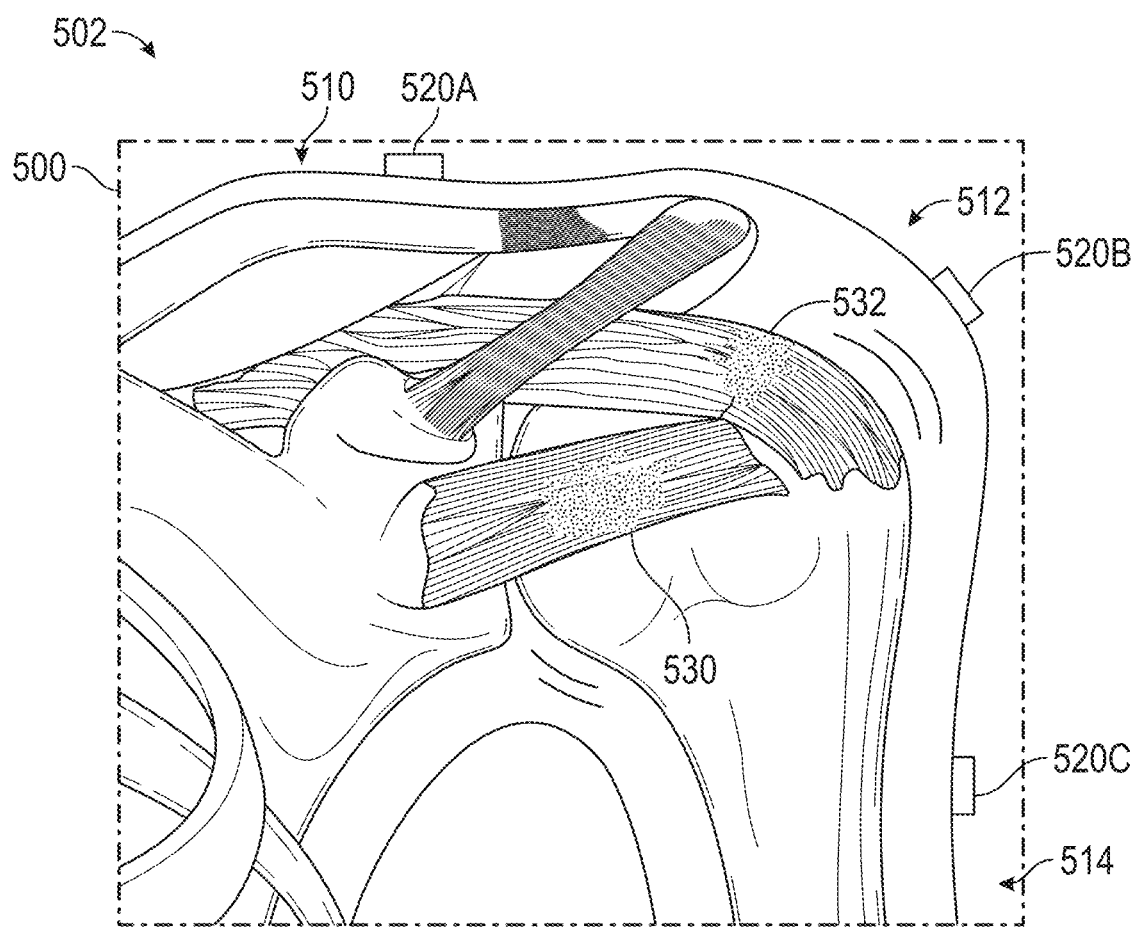
FIG. 5 is a transparent view (e.g., an image) of a body having one or more sensors attached thereto according to some aspects disclosed herein.

FIG. 5 is an image of a body of a subject 502 having one or more sensors (e.g., three are shown: 520A-520C) attached thereto according to some aspects disclosed herein. The subject 502 includes a collar 510, a shoulder 512, and an arm 514. The subject 502 also includes a ligament 530 and a tendon (e.g., the SST) 532.

The sensors 520A-520C can be attached to the subject 502 and configured to measure one or more parameters. As shown, the first sensor 520A can be attached to the collar 510, the second sensor 520B can be attached to the shoulder 512, and the third sensor 520C can be attached to the arm 514. In another implementation, one or more of the sensors 520A-520C (or another sensor) can be attached to the subject 502 (e.g., directly) above/outside the ligament 530 and/or tendon 532 to be monitored. The sensors 520A-520C can also or instead be attached to different locations on the subject 502 (e.g., the foot, the leg, the hip, the abdomen, the back, the neck, the head, etc.). In addition, although three sensors 520A-520C are shown, more or fewer sensors can be used. The parameters measured can be or include any of the input data described above (e.g., forceful exertion, posture, repetition, duration, vibration, etc.).

Figure 6:
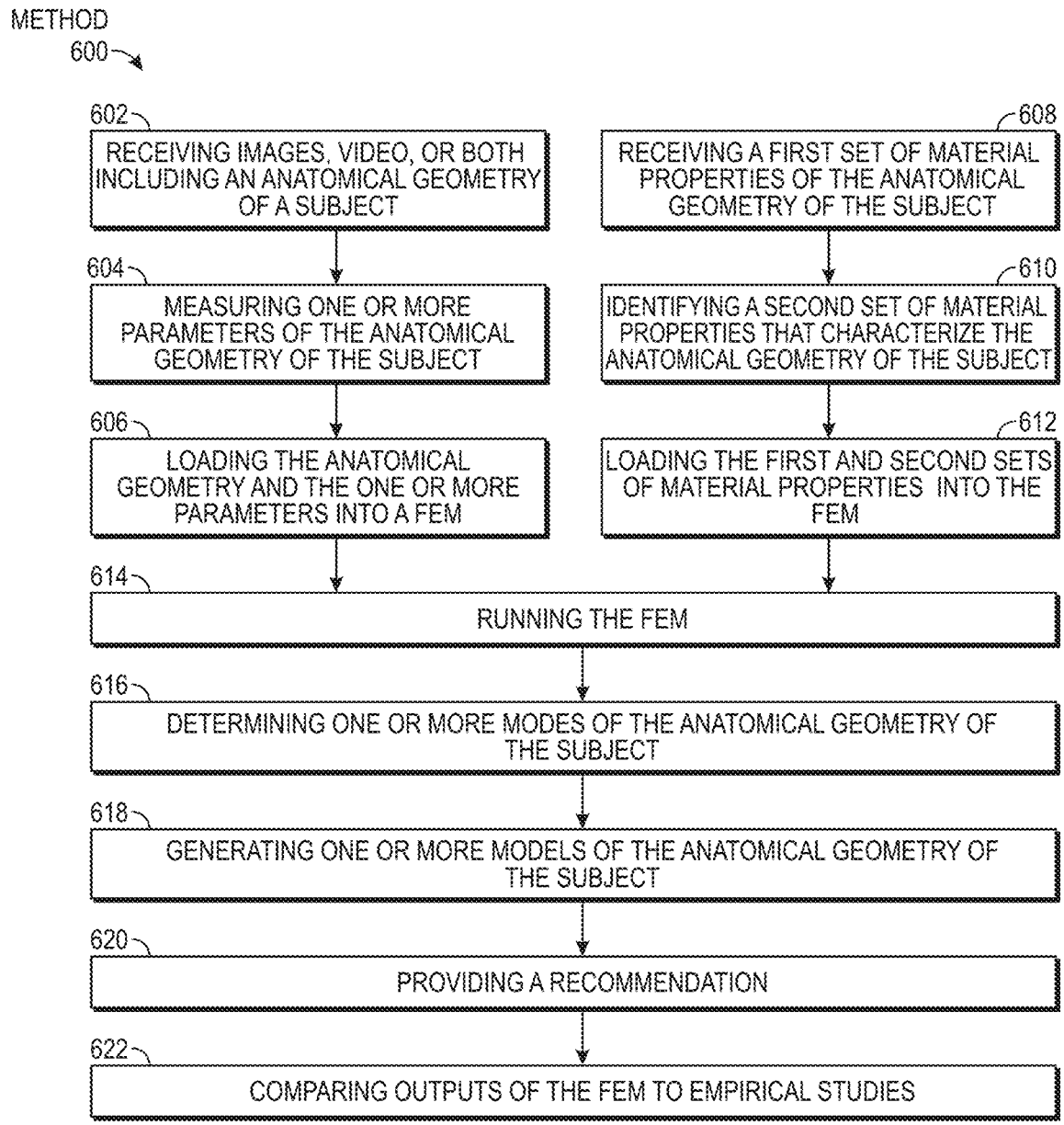
FIG. 6 is a flow chart depicting a method for modeling body tissue (e.g., soft tissue) according to some aspects disclosed herein.

FIG. 6 is a flow chart depicting a method 600 for modeling soft tissue, according to some aspects disclosed herein. The method 600 can monitor soft tissue to reduce the potential for injuries to those performing a (e.g., workplace) task. The method 600 can be partially implemented using the computing system 1200, as shown and described below in reference to FIG. 12. The method 600 further includes extra-computer actions that provide improvements in the field of industrial hygiene. Such actions include, for example, obtaining a repetitive stress data set related to the soft tissue and to the process (e.g., a description of force per area of the soft tissue and a number of repetitions) and implementing the guidelines to reduce the potential for repetitive stress injuries to an individual in a process.

An illustrative order of the method 600 is provided below. However, one or more steps of the method 600 can be performed in a different order, performed simultaneously, repeated, or omitted.

The method 600 can include receiving images, video, or both that include or show an anatomical geometry of a subject, as at 602. In one implementation, the anatomical geometry can be that of the particular subject (e.g., the particular person) being analyzed. In another implementation, the anatomical geometry can be that of other similar subjects (e.g., not the particular person being analyzed). The images and/or video can be or include magnetic resonance images (MRI), ultrasound images, computerized tomography images (CT scans), 3D scans, or a combination thereof. The anatomical geometry can be or include shapes and/or spatial linkages that describe the 2D and/or 3D anatomy being analyzed. As used herein, "shapes" can refer to the anatomy (e.g., soft tissue, bone, etc.), and/or the soft tissue changes (e.g., length, area, etc.) for a given task position (e.g., arm overhead extension versus resting at side). As used herein, "spatial linkages" refer to the limb and joint position relative to the rest of the body and the specific kinematics of the task. For example, a greater moment can be applied to joints during tasks requiring extension away from the body, or off-axis motions can induce shear forces. The anatomy can be a mammalian anatomy (e.g., a human anatomy); however, as described above, other types of anatomies are also contemplated herein. The anatomical geometry can help to create a foundational basis for defining motion paths of the anatomy and/or forces on the anatomy, which can be used to simulate workplace tasks.

The method 600 can also include measuring one or more parameters of the anatomical geometry of the subject, as at 604. The one or more parameters may or may not be measured using the images, video, or both. The one or more parameters can be measured while the subject performs a task (e.g., a workplace task). In one implementation, the parameters can be or include any of the input data described above, such as the ergonomic risk factors: forceful exertion, posture, repetition, duration, vibration, or a combination thereof. In another implementation, the subject can be exposed or subjected to one or more of the ergonomic risk factors, and the parameters can be or include a response of the soft tissue (e.g., strain, stress, etc.) in response to the ergonomic risk factor(s). This latter implementation can be used for detailed materials characterization (e.g., cadaver or surrogate DMA analysis) to obtain viscoelastic material properties that can be difficult to obtain from live test subjects.

The parameters can be measured by one or more of the sensors 520A-520C on the subject 502 (e.g., while the subject 502 performs a task). For example, a user (e.g., a worker) can have one or more tasks that form part of a manufacturing process (e.g., on an assembly line). The parameters can be used to define motion paths and expected forces on the anatomy, which can be used to characterize workplace tasks. The motion paths and forces can be applied to the anatomical geometry to produce a physical model that is ready to be integrated with material inputs.

The method 600 can also include loading or importing the anatomical geometry (from 602) and the one or more parameters (from 604) into a FEM (e.g., a computational framework), as at 606. The imported anatomical geometry (from 602) can include MRI images, ultrasound scans, and other imaging techniques. The imported anatomical geometry (from 602) can also include direct measurements from a living subject using ultrasound. As an example, the test subject shoulder can be scanned by ultrasound while the subject is standing upright with his/her arm fully extended in front, pressing against a target above his/her head while the applied force is measured. The ultra sound scanned images of a tendon can subsequently be digitized into the CAD geometry and imported into the FEM numerical engine. The same process can be repeated for different target positions relative to the shoulder of the subject as the applied force is also varied. By incorporating multiple measurements, the FEM predicts the stress and strain of the tendon for given changes in position and applied force.

The method 600 can also include receiving a first set of material properties of the anatomical geometry of the subject, as at 608. More particularly, this can include receiving a first set of material properties of the soft tissue of the subject. In one implementation, the first set of material properties can be measured in the particular subject (e.g., the particular person) being analyzed using external imaging techniques such as shear-wave elastography, ultrasound, or both. In another implementation, the first set of material properties can be measured in other similar subjects (e.g., not the particular person being analyzed) using the above-mentioned techniques. In yet another implementation, the first set of material properties can be received or derived from empirical studies or published research. The first set of material properties can be or include in-plane moduli, out-of-plane moduli, Poisson's ratio, or the like. The moduli can be linear, non-linear, or both.

The method 600 can also include identifying a second set of material properties that characterizes the anatomical geometry of the subject, as at 610. The second set of material properties can characterize the material properties of the soft tissue of the subject during the task. In an example, the second set of material properties can characterize the isotropic and/or anisotropic constituent properties of the soft tissue, the nonlinear behavior of the soft tissue, the estimated damage states of the soft tissue, or a combination thereof. In another example, a soft tissue material modulus can stiffen under higher loads, tendon extension, applied vibration, or a combination thereof. In response to this, anisotropic behavior of the soft tissue can occur, which can use a modulus definition in one or more vectors for complex motions paths and loading for various ranges of motion. Acute damage and healing of tendon fibers can also change the localized soft tissue material properties. If one or more material properties are not available, they can be measured from human test subjects or surrogates using external imaging techniques or a material sample composition technique such as dynamic mechanical analysis (DMA). For example, the second set of material properties can be measured using an external imaging technique or a material sample composition technique such as dynamic mechanical analysis (DMA).

The method 600 can also include loading or importing the received material properties (from 606) and the characterized material properties (from 608) into the FEM (e.g., the computational framework), as at 612. The FEM can be based on simple and/or complex material properties. The complex material properties can include, but are not limited to, nonlinearity, frequency dependent, viscoelasticity, orthotropy, or a combination thereof. For the FEM to be able to computationally predict the stress/strain state of the soft tissue (e.g., shoulder tendon) and its performance, the tendon material can first be numerically represented (as at 612) as an orthotropic material using/based on open literature material properties (from 606). For improved accuracy, use of a simple force/displacement characterization of the tendon material properties (from 608) can be integrated into the model. In another implementation, the accuracy can be improved by integrating a more complex viscoelastic characterization of the tendon material properties (from 610) into the model. The characterization can be performed directly on the tendon or indirectly through methods as described in 602. Direct characterization can be based at least partially upon cadaver tendons from different demographics or synthetic/surrogate versions of the tendons materials. Indirect characterization can be performed by utilizing medically published and accepted references (from 602) in order to indirectly measure the force/displacement or stress/strain of the tendon or part of the tendon (e.g., surface only).

Before executing or running the FEM (as describe below), the anatomical geometry (from 602) can first be meshed to account for the geometries (from 602) and the material orientations (from 608 to 612). The FEM can also have boundary conditions prescribed to allow the applied loads to act on the geometries (from 602). The applied loads in the FEM can be prescribed to follow a cyclic path to reproduce the physical observed cyclic motion of the subject represented in the method 600.

The method 600 can also include executing or running the FEM, as at 614. This can include computationally processing the FEM (e.g., an integrated physical and material model), which can be subsequently analyzed for outputs and trends of interest. The FEM can be executed/run using and/or based upon the anatomical geometry (from 602), the one or more parameters (from 604), the received material properties (from 606), the characterized material properties (from 608), or a combination thereof.

The method 600 can also include determining one or more modes of the anatomical geometry (e.g., the soft tissue) of the subject, as at 616. The modes can be determined based at least partially upon the running of the FEM. Thus, the modes can be determined based at least partially upon the anatomical geometry (from 602), the one or more parameters (from 604), the received material properties (from 606), the characterized material properties (from 608), or a combination thereof. The modes can be or include a stress mode, which refers to the stress on the anatomical geometry (e.g., the soft tissue) of the subject. The modes can also be or include a strain mode, which refers to the strain on the anatomical geometry (e.g., the soft tissue) of the subject. The modes can also be or include a vibration mode, which refers to natural frequencies that can exaggerate localized loading on the anatomy. For example, the vibration mode can refer to applied vibration from a power tool or similar device held by the subject while performing a task, which can translate to the soft tissue (e.g., shoulder tendon) as vibration tensioning or rubbing of the tendon against vibrating bones or other anatomical structure surrounding the tendon. The modes can also be or include a failure mode, which refers to progressive tissue damage. For example, the failure mode can refer to fatigue of the soft tissue (e.g., tendon), abrasion of the tendon surface due to rubbing, partial tarring of the tendon, and/or pinching of the nerve(s) neighboring the tendon.

In one implementation, the modes can be predictive (e.g., provide a forecast). In other words, the modes can predict the stress, strain, vibration, failure, etc. of the soft tissue at a future time if the task continues to be performed. For example, the modes can predict when the stress, strain, vibration, failure, etc. of the soft tissue will reach a predetermined level if the task continues.

The method 600 can also include generating one or more models of the anatomical geometry (e.g., the soft tissue) of the subject, as at 618. The models can be determined based at least partially upon the running of the FEM. Thus, the models can be determined based at least partially upon the anatomical geometry (from 602), the one or more parameters (from 604), the received material properties (from 606), the characterized material properties (from 608), or a combination thereof. Examples of the models are shown in FIGS. 7-11.

Figure 7:
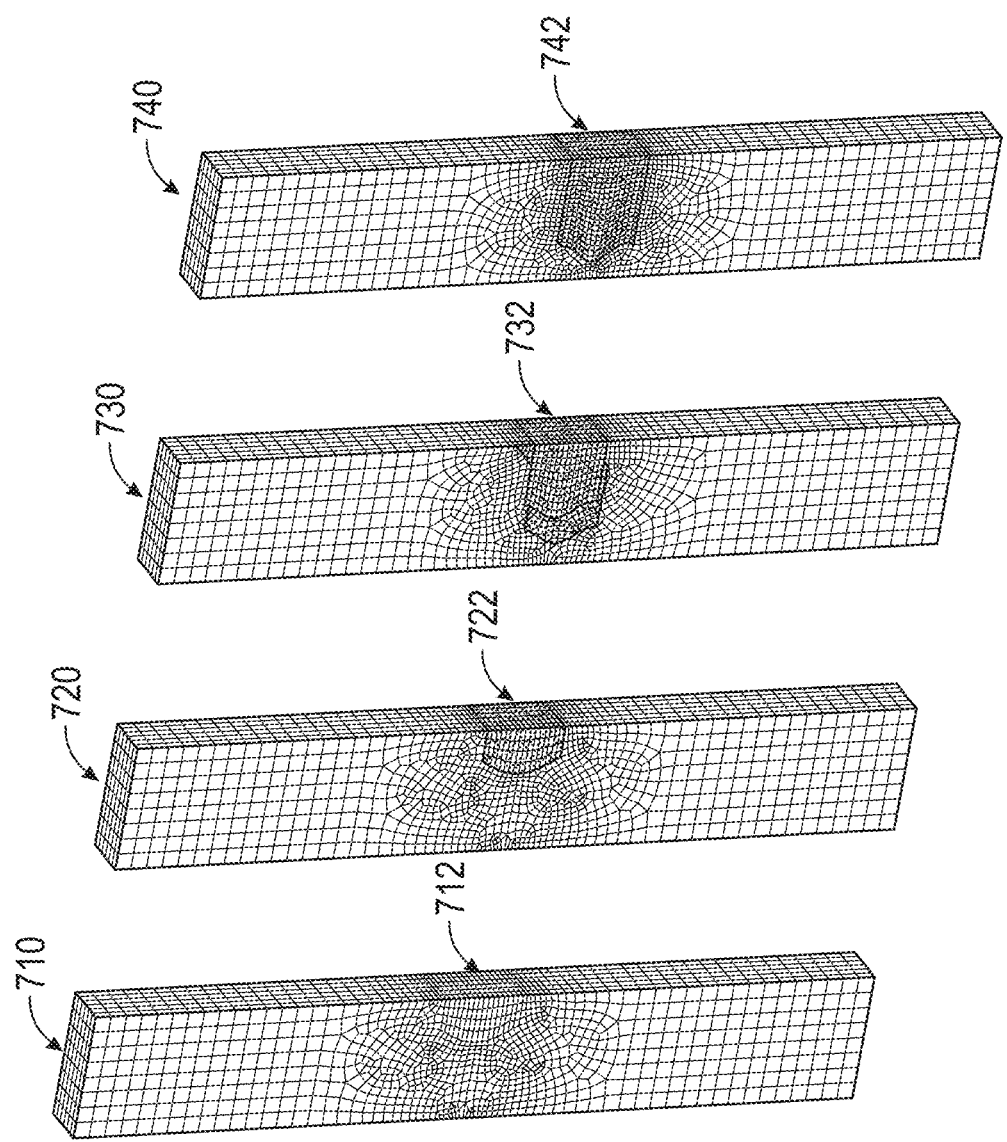
FIG. 7 shows models of a soft tissue segment with no healed damage zone, a soft tissue segment with a 2 mm×5 mm healed damage zone, a soft tissue segment with a 4 mm×5 mm healed damage zone, and a soft tissue segment with a 6 mm×5 mm healed damage zone, according to some aspects disclosed herein.

FIG. 7 shows models of a soft tissue segment 710 with no healed damage zone 712, a soft tissue segment 720 with a 2 mm×5 mm healed damage zone 722, a soft tissue segment 730 with a 4 mm×5 mm healed damage zone 732, and a soft tissue segment 740 with a 6 mm×5 mm healed damage zone 742, according to some aspects disclosed herein.

The soft tissue segment 710 can be a unidirectional laminate (uni-laminate) representation (e.g., 8 plies) with the $\in_{11}$ direction along the length of sample, and the soft tissue segments 720, 730, 740 can be quasi-isotropic (or quasi-symmetric) laminate representations in damaged and healed zones 722, 732, 742 only. The quasi-symmetric laminate representations are numerically represented by modeling a (45,90-45,0) s laminate stack, which numerical means that the laminate in the zones 722, 732, 742 is isotropic in the plane of the samples. The material uni-laminate ply property values are $\in_{11}$=140 MPa, $\in 22$=1 MPa, and $\in 33$=1 MPa, vs=0.497* (incompressible), G12=70 MPa (approximated), G13=70 MPa (approximated), and G23=70 MPa (approximated). The engineering elastic constant material properties $\in_{11} \in 22$, $\in 33$, and vs can be taken from medical journal publications, and the G12, G13 and G23 can be approximated to be half the value of $\in_{11}$. All nine simple engineering elastic constant material properties are required as FEM inputs in order to perform predictions. Classical lamination plate theory can be used to calculate effective elastic properties.

Figure 8:
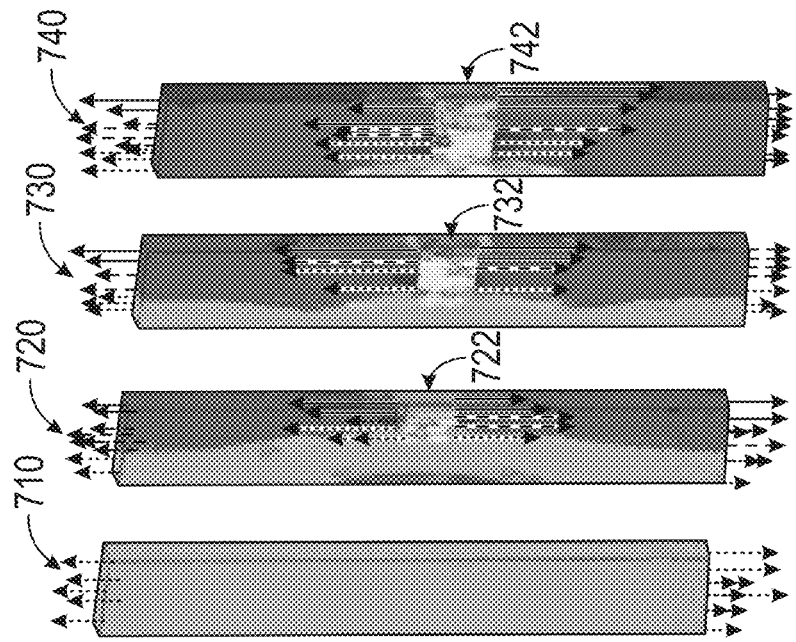
FIG. 8 shows models of strain on the soft tissue segments, according to some aspects disclosed herein.
Figure 8:
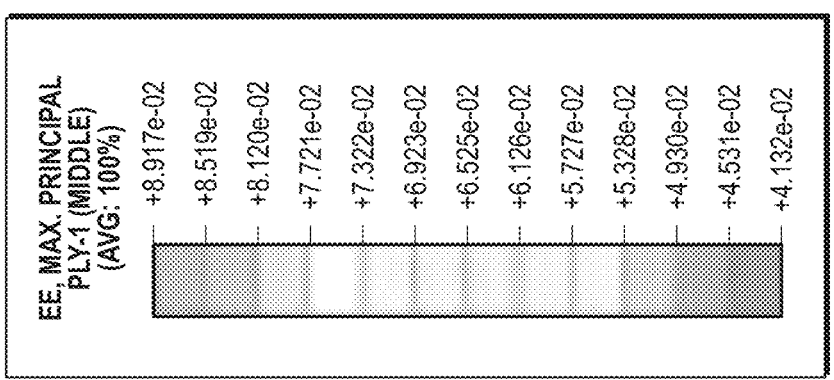
Figure 8:
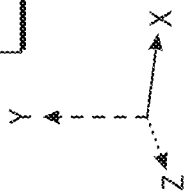

FIG. 8 shows models of strain on the soft tissue segments 710, 720, 730, 740, according to some aspects disclosed herein. The load is equivalent to 5% strain displacement along the length (e.g., 2.5 mm). The mechanical maximum principal strain is parallel to the load direction, as shown by the arrows. The tendon tissue can be treated as a composite material.

Figure 9:
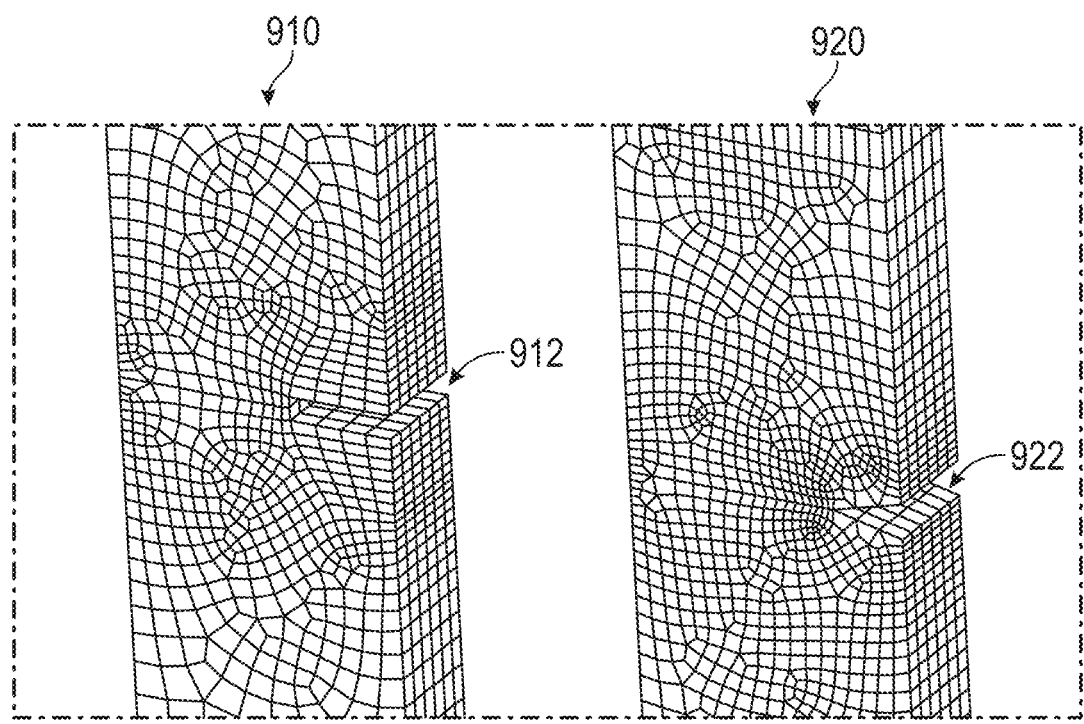
FIG. 9 shows models of a soft tissue segment with a 3 mm slot tear, and a soft tissue segment with 2 mm V-shaped tear, according to some aspects disclosed herein.

FIG. 9 shows models of a soft tissue segment 910 with a 3 mm slot tear 912, and a soft tissue segment 920 with 2 mm V-shaped tear 922, according to some aspects disclosed herein.

Figure 10:
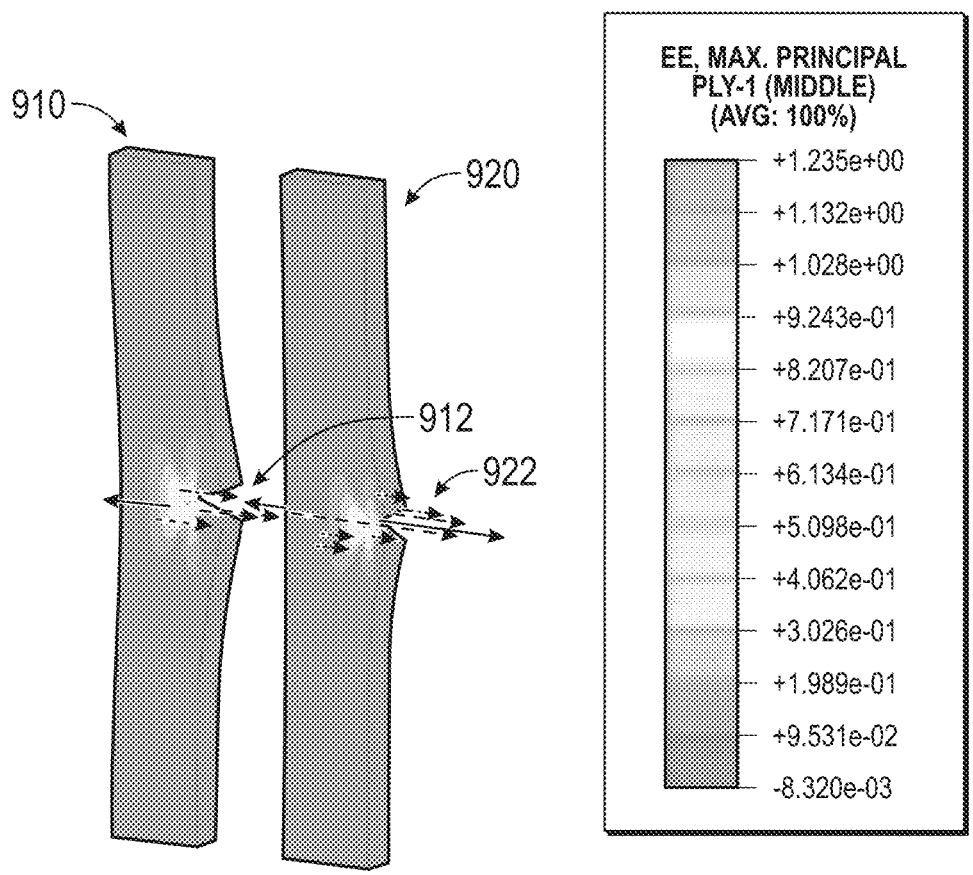
FIG. 10 shows models of strain on the soft tissue segments, according to some aspects disclosed herein.
Figure 10:
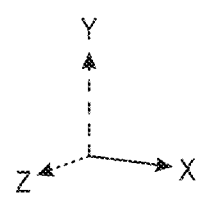

FIG. 10 shows models of strain on the soft tissue segments 910, 920, according to some aspects disclosed herein. The load is equivalent to 5% strain displacement along the length (e.g., 2.5 mm). The mechanical maximum principal strain is perpendicular to the load direction, as shown by the arrows. The mechanical strain can be large due to material properties in the perpendicular direction, which can cause tears. Shoulder joint instability can cause more force on the rotator cuff tendons, which are designed to move the shoulder joint, not stabilize it. This can cause the tendons to degenerate and become weaker, which makes them tear more easily. The rotator cuff tear is the symptom of shoulder joint instability, the underlying true missing diagnosis.

Figure 11:
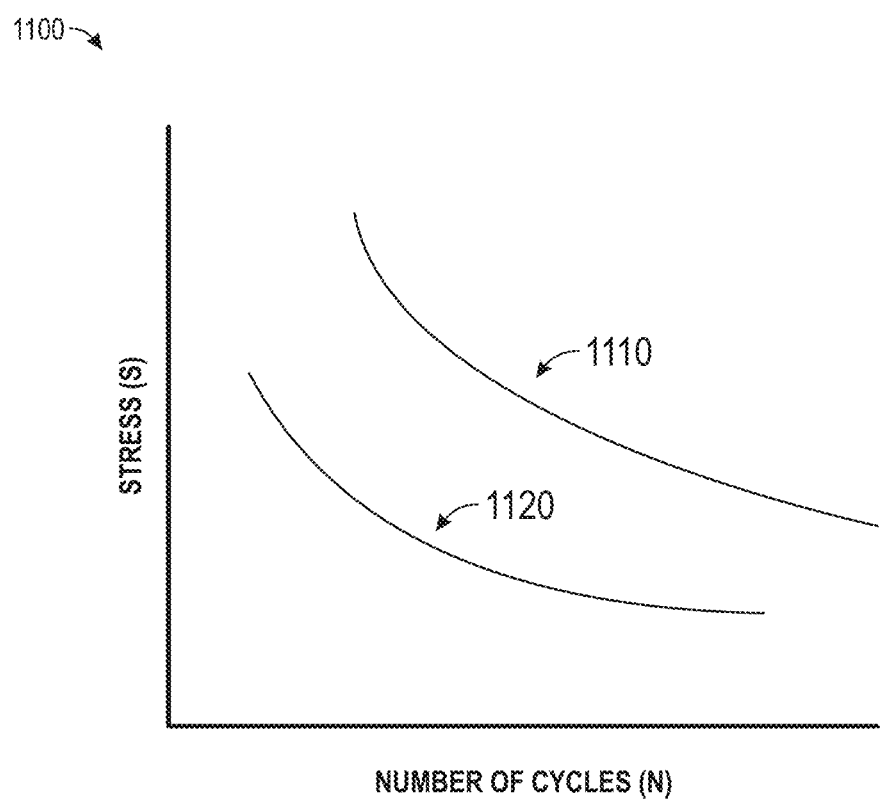
FIG. 11 is a graph including one or more S-N fatigue curves for the anatomical geometry (e.g., the soft tissue) of the subject according to some aspects disclosed herein.

FIG. 11 is a graph 1100 including one or more S-N fatigue curves 1110, 1120 for the anatomical geometry (e.g., the soft tissue) of the subject according to some aspects disclosed herein. The graph 1100 plots the magnitude of a cyclic stress (S) against the logarithmic scale of cycles to failure (N). In other words, the graph 1100 can show the predicted number of cycles to failure for a given repetitive loading pattern. In one example, the S-N fatigue curve 1110 can represent healthy tendons for a given task, and the S-N fatigue curve 1120 can represent damaged tendons for the given task. In another example, the S-N fatigue curve 1110 can represent no vibration during a given task, and the S-N fatigue curve 1120 can represent applied vibration during the given task. Incorporating multiple inputs in varying degrees can result in more complex curves, which can be overlaid for comparison. Curves can also or instead be generated for different task postures (e.g., 25% overhead extension, 50% overhead extension, 75% overhead extension, 100% overhead extension, sitting, standing, etc.).

Instead of or in addition to the S-N fatigue curve(s), the FEM can output an assessment of one or more (e.g., four) regimes of tissue damage: no damage, sub-rupture, partial damage, full damage. The FEM can also or instead output a comparison of various changes to work procedures and tools (e.g., evaluate reduced range-of-motion, power tools of different weights and vibration frequencies, introduction of ergonomic assist devices, etc.), which can lead to optimized task design guidance and/or recommended work intervals for a given task.

The method 600 can also include providing a recommendation, as at 620. The recommendation can be based at least partially upon running of the FEM (from 614), the one or more modes (from 616), the models (from 618), or both. For example, the recommendation can be based at least partially upon the stress on the soft tissue, the strain on the soft tissue, or both. The recommendation can be specifically tailored to the anatomical geometry of the subject. In one implementation, recommendation can be specifically tailored to the particular subject (e.g., whose parameters are measured at 604). In another implementation, the recommendation can also or instead be specifically tailored to different (e.g., all) subjects that can perform the task. The recommendation can provide a limit on the task being performed to prevent the subject from damaging the soft tissue. For example, the recommendation can limit the amount of weight to be lifted during the task, the number of times the task is to be performed (e.g., repetitions), the amount of time to perform the task, or a combination thereof.

As a result, the recommendation can help to ameliorate repetitive stress injuries of workers performing a part of a manufacturing process. Alternately, the method 600 can be used to ameliorate repetitive stress injuries of an athlete executing a training program. The athlete can have one or more exercises that form part of the training program. The exercises can be modified by the recommendation produced by the method 600. In general, the method 600 can be practiced to ameliorate repetitive stress injuries in any type of process that includes repetitive movements by a person, not limited to manufacturing or athletic processes.

The method 600 can be used to ameliorate injuries to any of a variety of soft tissues. According to some examples, the method 600 can be used to ameliorate injuries to tendons or tendon complexes. Examples of such tendons and tendon complexes are presented above in reference to FIGS. 1-3. Alternately, the method 600 can be used to ameliorate injuries to connective tissue or musculoskeletal soft tissue. In general, non-limiting examples of soft tissues for which examples can be implemented include tendons, tendon complexes, intervertebral (spinal) discs, and ligaments.

The method 600 can also include comparing outputs of the FEM to empirical studies, as at 622. For example, this can include comparing the modes (from 616) and/or the models (from 618) to repetitive stress data in empirical studies. This can help to verify the accuracy of the outputs of the FEM. The method 600 can then look back to step 614, where the FEM can be executed or run again (iteratively). In one implementation, the FEM can be modified (e.g., refined) based at least partially upon the comparison (from 622) such that the additional iteration(s) of the FEM yield(s) different (e.g., more accurate) outputs.

Figure 12:
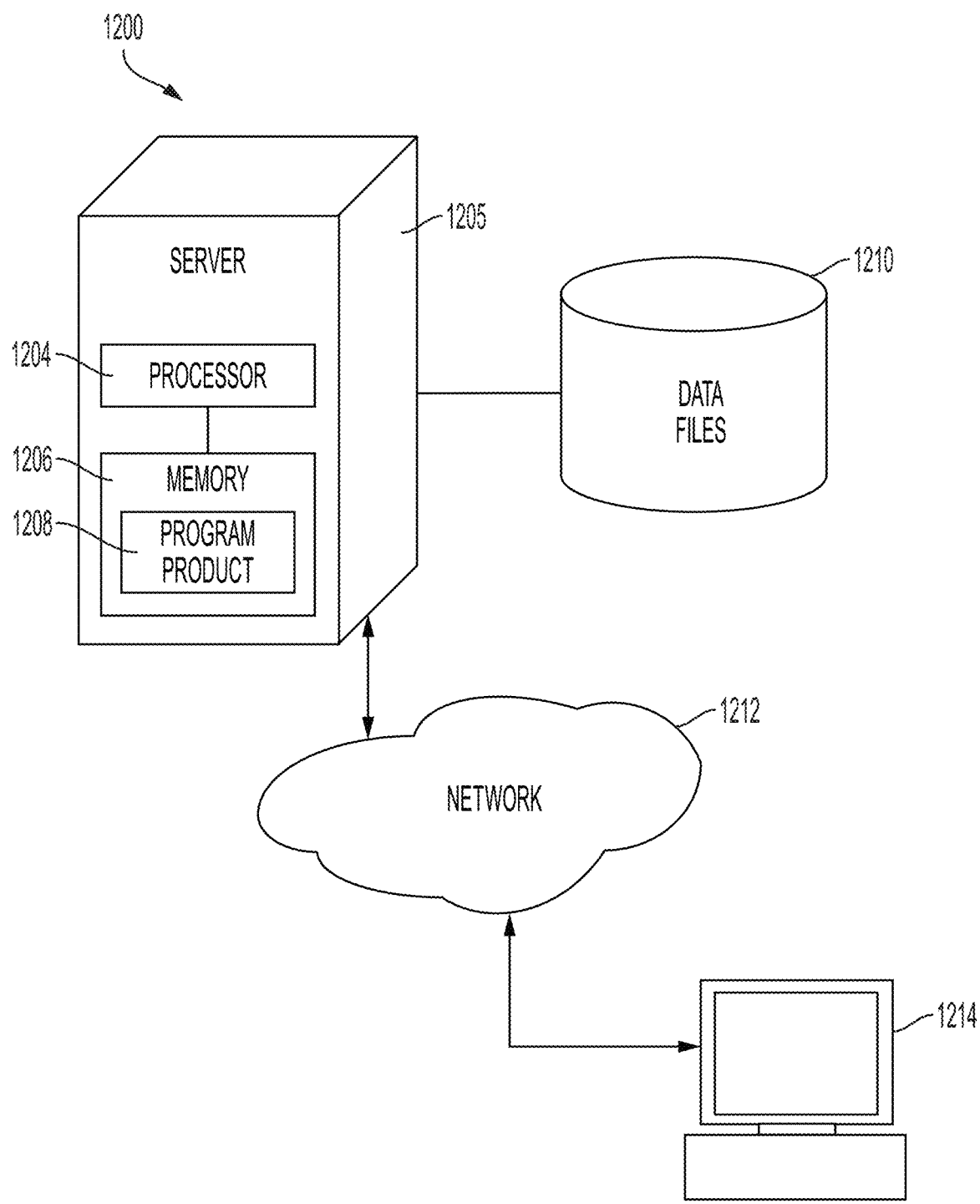
FIG. 12 is a schematic view of a computing system for performing at least a portion of the method(s) disclosed herein according to some aspects disclosed herein.

The present disclosure also provides various systems and computer program products or machine readable media. In some aspects, for example, the methods described herein are optionally performed or facilitated at least in part using systems, distributed computing hardware and applications (e.g., cloud computing services), electronic communication networks, communication interfaces, computer program products, machine readable media, electronic storage media, software (e.g., machine-executable code or logic instructions) and/or the like. To illustrate, FIG. 12 provides a schematic diagram of an exemplary system suitable for use with implementing at least aspects of the methods disclosed in this application. As shown, system 1200 includes at least one controller or computer, e.g., server 1205 (e.g., a search engine server), which includes processor 1204 and memory, storage device, or memory 1206, and one or more other communication devices 1214 (e.g., client-side computer terminals, telephones, tablets, laptops, other mobile devices, etc.) positioned remote from and in communication with the server 1205, through electronic communication network 1212, such as the Internet or other internetwork. Communication device 1214 typically includes an electronic display (e.g., an internet enabled computer or the like) in communication with, e.g., server 1205 computer over network 1212 in which the electronic display comprises a user interface (e.g., a graphical user interface (GUI), a web-based user interface, and/or the like) for displaying results upon implementing the methods described herein. In certain aspects, communication networks also encompass the physical transfer of data from one location to another, for example, using a hard drive, thumb drive, or other data storage mechanism. System 1200 also includes program product 1208 stored on a computer or machine readable medium, such as, for example, one or more of various types of memory, such as memory 1206 of server 1205, that is readable by the server 1205, to facilitate, for example, an executable by one or more other communication devices, such as communication device 1214 (e.g., schematically shown as a desktop or personal computer). In some aspects, system 1200 optionally also includes at least one database server, such as, for example, server 1210 associated with an online website having data stored thereon (e.g., control sample or comparator result data, indexed customized therapies, etc.) searchable either directly or through server 1205. System 1200 optionally also includes one or more other servers positioned remotely from server 1205, each of which are optionally associated with one or more database servers 1210 located remotely or located local to each of the other servers. The other servers can beneficially provide service to geographically remote users and enhance geographically distributed operations.

As understood by those of ordinary skill in the art, memory 1206 of the server 1205 optionally includes volatile and/or nonvolatile memory including, for example, RAM, ROM, and magnetic or optical disks, among others. It is also understood by those of ordinary skill in the art that although illustrated as a single server, the illustrated configuration of server 1205 is given only by way of example and that other types of servers or computers configured according to various other methodologies or architectures can also be used. Server 1205 shown schematically in FIG. 12, represents a server or server cluster or server farm and is not limited to any individual physical server. The server site can be deployed as a server farm or server cluster managed by a server hosting provider. The number of servers and their architecture and configuration can be increased based on usage, demand and capacity requirements for the system 1200. As also understood by those of ordinary skill in the art, communication device 1214 (e.g., a computer) in these aspects, for example, can be a laptop, desktop, tablet, personal digital assistant (PDA), cell phone, server, or other types of computers. As known and understood by those of ordinary skill in the art, network 1212 can include an internet, intranet, a telecommunication network, an extranet, or world wide web of a plurality of computers/servers in communication with one or more other computers through a communication network, and/or portions of a local or other area network.

As further understood by those of ordinary skill in the art, exemplary program product or program product 1208 is optionally in the form of microcode, programs, cloud computing format, routines, and/or symbolic languages that provide one or more sets of ordered operations that control the functioning of the hardware and direct its operation. Program product 1208, according to an exemplary aspect, also need not reside in its entirety in volatile memory, but can be selectively loaded, as necessary, according to various methodologies as known and understood by those of ordinary skill in the art.

As further understood by those of ordinary skill in the art, the term "computer-readable medium" or "machine-readable medium" refers to any medium that participates in providing instructions to a processor for execution. To illustrate, the term "computer-readable medium" or "machine-readable medium" encompasses distribution media, cloud computing formats, intermediate storage media, execution memory of a computer, and any other medium or device capable of storing program product 1208 implementing the functionality or processes of various aspects of the present disclosure, for example, for reading by a computer. A "computer-readable medium" or "machine-readable medium" can take many forms, including but not limited to, non-volatile media, volatile media, and transmission media. Non-volatile media includes, for example, optical or magnetic disks. Volatile media includes dynamic memory, such as the main memory of a given system. Transmission media includes coaxial cables, copper wire and fiber optics, including the wires that comprise a bus. Transmission media can also take the form of acoustic or light waves, such as those generated during radio wave and infrared data communications, among others. Exemplary forms of computer-readable media include a floppy disk, a flexible disk, hard disk, magnetic tape, a flash drive, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave, or any other medium from which a computer can read.

Program product 1208 is optionally copied from the computer-readable medium to a hard disk or a similar intermediate storage medium. When program product 1208, or portions thereof, are to be run, it is optionally loaded from their distribution medium, their intermediate storage medium, or the like into the execution memory of one or more computers, configuring the computer(s) to act in accordance with the functionality or method of various aspects. All such operations are well known to those of ordinary skill in the art of, for example, computer systems.

To further illustrate, in certain aspects, this application provides systems that include one or more processors, and one or more memory components in communication with the processor. The memory component may include one or more instructions that, when executed, cause the processor to perform operations. The operations may include receiving one or more images that include an anatomical geometry of a subject. The operations may also include measuring or receiving a plurality of parameters of the anatomical geometry of the subject using one or more sensors attached to the subject. The operations may also include receiving a first set of material properties for the soft tissue of the subject. The operations may also include identifying a second set of material properties that characterizes the soft tissue while the subject performs a task. The operations may also include may also determining a strain on the soft tissue, a stress on the soft tissue, or both based at least partially upon the one or more images, the parameters, the first set of material properties, and the second set of material properties.

System 1200 also typically includes additional system components that are configured to perform various aspects of the methods described herein. In some of these aspects, one or more of these additional system components are positioned remote from and in communication with server 1205 through electronic communication network 1212, whereas in other aspects, one or more of these additional system components are positioned local, and in communication with server 1205 (i.e., in the absence of electronic communication network 1212) or directly with, for example, communication device 1214 (e.g., a computer).

All documents described herein are incorporated by reference herein, including any priority documents and/or testing procedures to the extent they are not inconsistent with this text. As is apparent from the foregoing general description and the specific aspects, while forms of the aspects have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group consisting of," or "I"" preceding the recitation of the composition, element, or elements and vice versa, e.g., the terms "comprising," "consisting essentially of," "consisting of" also include the product of the combinations of elements listed after the term.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, systems, and/or component parts or other aspects thereof can be used in various combinations. All patents, patent applications, websites, other publications or documents, and the like cited herein are incorporated by reference in their entirety for all purposes to the same extent as if each individual item were specifically and individually indicated to be so incorporated by reference.

What is claimed is:

1. A method for modeling soft tissue, comprising:
   receiving one or more images comprising an anatomical geometry of a first subject, wherein the anatomical geometry comprises a soft tissue;
   measuring a plurality of parameters of the anatomical geometry of the first subject using one or more sensors attached to the first subject;
   receiving a first set of material properties for the soft tissue of the first subject, a second subject, or both;
   identifying a second set of material properties that characterizes the soft tissue while the first subject performs a task, wherein the second set of material properties is different than the first set of material properties, and wherein the task comprises a repetitive task that is part of an assembly line;
   determining a strain on the soft tissue, a stress on the soft tissue, or both based at least partially upon the one or more images, the parameters, the first set of material properties, and the second set of material properties; and
   modifying performance of the task in response to the strain, the stress, or both, wherein the task is modified to limit a number of times that the task is performed or an amount of time to perform the task.

2. The method of claim 1, wherein the images comprise magnetic resonance images, computerized tomography images, ultrasound images, or a combination thereof, and wherein the first subject comprises a living mammal.

3. The method of claim 1, wherein the parameters are measured while the first subject performs the task.

4. The method of claim 1, wherein the parameters comprise forceful exertion, posture, repetition, duration, vibration, or a combination thereof.

5. The method of claim 1, wherein the parameters describe a behavior of the soft tissue in response to the first subject being exposed to forceful exertion, posture, repetition, duration, vibration, or a combination thereof during performance of the task.

6. The method of claim 1, wherein the first set of material properties comprises in-plane moduli, out-of-plane moduli, and Poisson's ratio.

7. The method of claim 1, wherein the second set of material properties comprises an isotropic property of the soft tissue, an anisotropic property of the soft tissue, a nonlinear behavior of the soft tissue, and an estimated damage state of the soft tissue.

8. The method of claim 1, further comprising generating a model that describes the soft tissue based at least partially upon the strain, the stress, or both.

9. The method of claim 8, wherein the model comprises a 3D model of the soft tissue, and wherein the model identifies a direction of a load on the soft tissue during the task and a direction of the strain, the stress, or both.

10. The method of claim 8, wherein the model comprises a S-N fatigue curve that predicts a number of cycles performed by the first subject during the task before the soft tissue is damaged.

11. A method for modeling soft tissue, comprising:
receiving one or more images comprising an anatomical geometry of a subject, wherein the images comprise magnetic resonance images, computerized tomography images, ultrasound images, or a combination thereof, wherein the anatomical geometry comprises soft tissue, and wherein the subject comprises a living mammal;
measuring a plurality of parameters of the anatomical geometry of the subject, wherein the parameters are measured using one or more sensors attached to the subject, wherein the parameters are measured while the subject performs a task, wherein the task comprises a repetitive task that is part of an assembly line, and wherein the parameters comprise forceful exertion, posture, repetition, duration, and vibration;
receiving a first set of material properties for the soft tissue of the subject, wherein the first set of material properties comprises in-plane moduli, out-of-plane moduli, Poisson's ratio, or a combination thereof;
identifying a second set of material properties that characterizes the soft tissue during the task, wherein the second set of material properties is different than the first set of material properties, wherein the second set of material properties comprises an isotropic property of the soft tissue, an anisotropic property of the soft tissue, a nonlinear behavior of the soft tissue, an estimated damage state of the soft tissue, or a combination thereof;
running a finite element model based at least partially upon the one or more images, the parameters, the first set of material properties, and the second set of material properties;
determining a strain on the soft tissue, a stress on the soft tissue, or both based at least partially upon the running of the finite element model;
generating a model that describes the soft tissue based at least partially upon the determined strain, the determined stress, or both; and
modifying performance of the task in response to the model, wherein the task is modified to limit a number of times that the task is performed or an amount of time to perform the task.

12. The method of claim 11, wherein the first set of material properties is measured using shear-wave elastography, ultrasound, or both.

13. The method of claim 11, wherein the second set of material properties is measured using an external imaging technique, a material sample composition technique, or both.

14. The method of claim 11, wherein the model comprises:
a first S-N fatigue curve that describes the soft tissue when healthy; and
a second S-N fatigue curve that describes a state of the soft tissue in response to the task.

15. The method of claim 11, further comprising providing a recommendation that provides a limit on the task being performed by the subject to prevent the subject from damaging the soft tissue, wherein the recommendation is based at least partially upon the stress on the soft tissue, the strain on the soft tissue, or both.

16. The method of claim 11, wherein the task involves use of a power tool that causes the soft tissue to vibrate.

17. The method of claim 16, further comprising determining a vibration mode based at least partially upon the running of the finite element model, wherein the vibration mode comprises frequencies that exaggerate localized loading on the soft tissue due to the vibration from the power tool.

18. The method of claim 17, wherein the localized loading comprises the soft tissue tensioning or rubbing against an adjacent bone.

19. The method of claim 16, wherein the model comprises:
a first S-N curve that represents the soft tissue while the task is being performed with no vibration;
a second S-N curve that represents the soft tissue while the task is being performed with vibration at a first frequency; and
a third S-N curve that represents the soft tissue while the task is being performed with vibration at a second frequency that is different than the first frequency.

20. A system for characterizing a behavior of soft tissue in a mammal, the system comprising:
a plurality of sensors that are configured to be attached to a human subject, wherein the sensors are configured to measure a plurality of parameters while the human subject performs a repetitive task, wherein the repetitive task is part of an assembly line, and wherein the parameters comprise forceful exertion, posture, repetition, duration, and vibration; and
a computing system configured to perform operations, the operations comprising:
receiving one or more images comprising an anatomical geometry of the human subject, wherein the images comprise magnetic resonance images, computerized tomography images, and ultrasound images, wherein the anatomical geometry comprises soft tissue;
receiving the parameters from the sensors;
receiving a first set of material properties for the soft tissue of the human subject, wherein the first set of material properties comprises in-plane linear moduli, out-of-plane linear moduli, and Poisson's ratio;
identifying a second set of material properties that characterizes the soft tissue during the repetitive task, wherein the second set of material properties is different than the first set of material properties, wherein the second set of material properties comprises an isotropic property of the soft tissue, an anisotropic property of the soft tissue, a nonlinear behavior of the soft tissue, and an estimated damage state of the soft tissue;
running a finite element model based at least partially upon the one or more images, the parameters, the first set of material properties, and the second set of material properties;
predicting a strain mode, a stress mode, a vibration mode, and a failure mode of the soft tissue based at least partially upon the running of the finite element model;
generating a model that describes the soft tissue based at least partially upon the strain mode, the stress mode, the vibration mode, the failure mode, or a combination thereof; and
modifying performance of the repetitive task in response to the model, wherein the task is modified to limit a number of times that the repetitive task is performed or an amount of time to perform the repetitive task.

\* \* \* \* \*